US008162914B2

(12) United States Patent
Kraushaar et al.

(10) Patent No.: US 8,162,914 B2
(45) Date of Patent: Apr. 24, 2012

(54) CAP ADAPTERS FOR MEDICAMENT VIAL AND ASSOCIATED METHODS

(76) Inventors: Timothy Y. Kraushaar, Seal Beach, CA (US); Willard K. Kelsey, Palm Desert, CA (US)

( * ) Notice: Subject to any disclaimer, the term of this patent is extended or adjusted under 35 U.S.C. 154(b) by 474 days.

(21) Appl. No.: 12/368,797

(22) Filed: Feb. 10, 2009

(65) Prior Publication Data

US 2010/0204671 A1 Aug. 12, 2010

(51) Int. Cl.
*A61M 5/32* (2006.01)

(52) U.S. Cl. ........................................ 604/414; 604/411

(58) Field of Classification Search ........... 604/411–416
See application file for complete search history.

(56) References Cited

U.S. PATENT DOCUMENTS

| | | | | |
|---|---|---|---|---|
| 3,542,240 A | | 11/1970 | Solowey | |
| 3,740,543 A | * | 6/1973 | Franc | 446/147 |
| 3,783,895 A | | 1/1974 | Weichselbaum | |
| 3,797,521 A | * | 3/1974 | King | 137/858 |
| 3,826,261 A | | 7/1974 | Killinger | |
| 3,885,607 A | | 5/1975 | Peltier | |
| 3,977,555 A | | 8/1976 | Larson | |
| 4,262,671 A | | 4/1981 | Kersten | |
| 4,396,016 A | | 8/1983 | Becker | |
| 4,440,207 A | | 4/1984 | Genatempo et al. | |
| 4,475,915 A | | 10/1984 | Sloane | |
| 4,507,113 A | * | 3/1985 | Dunlap | 604/71 |
| 4,684,365 A | * | 8/1987 | Reinicke | 604/126 |
| 4,820,276 A | | 4/1989 | Moreno | |
| 4,857,068 A | | 8/1989 | Kahn | |
| 4,997,430 A | | 3/1991 | Van der Heiden et al. | |
| 5,017,186 A | | 5/1991 | Arnold | |
| 5,102,406 A | | 4/1992 | Arnold | |

(Continued)

FOREIGN PATENT DOCUMENTS

WO WO 00/35517 6/2000

OTHER PUBLICATIONS

Non-Final Office Action on co-pending U.S. Appl. No. 12/368,791 dated Jun. 23, 2011.

(Continued)

*Primary Examiner* — Leslie Deak
*Assistant Examiner* — Susan Su
(74) *Attorney, Agent, or Firm* — Klein, O'Neill & Singh, LLP

(57) ABSTRACT

Cap adapters for a medicament vial configured to facilitate the transfer of liquid medicament from the vial and into a syringe. In one embodiment the cap adapter comprises a wall portion with a first lumen passing through it. A vial-engaging portion secures the cap adapter to the vial. A spike extends from the wall portion and defines a second lumen passing through the wall portion. A cone-shaped shield extends from the first lumen. The shield is configured to guide a hypodermic needle toward the first lumen to thereby reduce a risk of needlestick to a user handling the vial. In certain embodiments, a light source cooperates with the cap adapter to illuminate at least a portion of the cap adapter to reduce a risk of needlestick to a user handling the vial in a darkened environment. In certain embodiments, a secondary sealing member abuts a first face of the wall portion and seals an end of the first lumen. In certain embodiments, a locking sleeve resists or prevents removal of the cap adapter from the medicament vial.

18 Claims, 24 Drawing Sheets

U.S. PATENT DOCUMENTS

| | | | | |
|---|---|---|---|---|
| 5,169,602 | A | 12/1992 | Pang et al. | |
| 5,354,287 | A * | 10/1994 | Wacks | 604/232 |
| 5,377,725 | A * | 1/1995 | Neff | 141/27 |
| 5,397,303 | A * | 3/1995 | Sancoff et al. | 604/82 |
| 5,520,659 | A | 5/1996 | Hedges | |
| 5,776,116 | A * | 7/1998 | Lopez et al. | 604/533 |
| 5,817,082 | A | 10/1998 | Niedospial, Jr. et al. | |
| 5,827,262 | A * | 10/1998 | Neftel et al. | 604/414 |
| 5,890,610 | A * | 4/1999 | Jansen et al. | 215/253 |
| 5,895,383 | A | 4/1999 | Niedospial, Jr. | |
| 5,902,298 | A | 5/1999 | Niedospial, Jr. et al. | |
| 6,039,093 | A * | 3/2000 | Mrotzek et al. | 141/386 |
| 6,139,534 | A * | 10/2000 | Niedospial et al. | 604/411 |
| 6,343,629 | B1 | 2/2002 | Wessman et al. | |
| 6,409,708 | B1 | 6/2002 | Wessman | |
| 6,478,788 | B1 * | 11/2002 | Aneas | 604/411 |
| 6,551,299 | B2 * | 4/2003 | Miyoshi et al. | 604/403 |
| 6,558,365 | B2 | 5/2003 | Zinger et al. | |
| 6,699,229 | B2 | 3/2004 | Zinger et al. | |
| 6,875,205 | B2 | 4/2005 | Leinsing | |
| 6,890,328 | B2 | 5/2005 | Fowles et al. | |
| 6,997,917 | B2 | 2/2006 | Niedospial, Jr. et al. | |
| 7,032,631 | B2 * | 4/2006 | Py | 141/82 |
| 7,086,431 | B2 | 8/2006 | D'Antonio et al. | |
| 7,192,423 | B2 | 3/2007 | Wong | |
| 7,306,584 | B2 * | 12/2007 | Wessman et al. | 604/500 |
| D561,348 | S | 2/2008 | Zinger et al. | |
| 7,354,427 | B2 * | 4/2008 | Fangrow | 604/413 |
| 7,491,197 | B2 * | 2/2009 | Jansen et al. | 604/413 |
| 7,507,227 | B2 * | 3/2009 | Fangrow | 604/414 |
| 7,632,261 | B2 * | 12/2009 | Zinger et al. | 604/414 |
| 7,753,095 | B2 * | 7/2010 | Kiani et al. | 141/330 |
| 7,810,529 | B2 * | 10/2010 | Py | 141/329 |
| 2002/0099355 | A1 * | 7/2002 | Chen | 604/412 |
| 2003/0069543 | A1 * | 4/2003 | Carpenter et al. | 604/190 |
| 2003/0070726 | A1 * | 4/2003 | Andreasson et al. | 141/329 |
| 2003/0206409 | A1 * | 11/2003 | Parsons et al. | 362/183 |
| 2005/0030740 | A1 * | 2/2005 | Kumthampinij et al. | 362/157 |
| 2005/0251102 | A1 * | 11/2005 | Hegland et al. | 604/500 |
| 2007/0106244 | A1 | 5/2007 | Mosler et al. | |
| 2007/0212922 | A1 * | 9/2007 | Montena et al. | 439/352 |
| 2008/0009789 | A1 * | 1/2008 | Zinger et al. | 604/89 |
| 2009/0069783 | A1 * | 3/2009 | Ellstrom et al. | 604/415 |
| 2009/0216212 | A1 * | 8/2009 | Fangrow, Jr. | 604/406 |
| 2010/0114058 | A1 * | 5/2010 | Weitzel et al. | 604/411 |
| 2011/0144614 | A1 * | 6/2011 | Hereford | 604/414 |

OTHER PUBLICATIONS

International Search Report on corresponding PCT application (PCT/US2010/023488) from International Searching Authority (KIPO) dated Nov. 15, 2010.

Written Opinion on corresponding PCT application (PCT/US2010/023488) from International Searching Authority (KIPO) dated Nov. 15, 2010.

* cited by examiner

CAP ADAPTERS FOR MEDICAMENT VIAL AND ASSOCIATED METHODS

CROSS-REFERENCE TO RELATED APPLICATIONS

The disclosure of the present application shares common subject matter with the disclosure of application Ser. No. 12/368,791, filed on Feb. 10, 2009.

FEDERALLY SPONSORED RESEARCH OR DEVELOPMENT

Not applicable

BACKGROUND

The present invention relates to devices and methods for withdrawing medicament from a vial.

A typical medicament vial includes an enlarged mouth portion forming an access port for removing liquid medicament from the vial. The mouth portion includes an opening that is sealed by a stopper made of an elastomeric material, such as butyl rubber. A closure, typically formed of metal, is crimped over the enlarged mouth portion and the stopper to positively hold the stopper against the opening. The closure has an aperture to expose a central portion of the stopper. To withdraw the liquid medicament from the vial, a syringe needle pierces the stopper to position the distal end of the needle within the liquid medicament inside the vial. Drawing back on the syringe plunger draws liquid out of the vial and into the syringe barrel.

SUMMARY

This disclosure describes various embodiments of a medicament vial cap adapter configured to facilitate the transfer of a liquid medicament from a vial to a syringe. These embodiments have several features, no single one of which is solely responsible for the desirable attributes of these embodiments. Without limiting the scope of the present embodiments as expressed by the claims that follow, their more prominent features now will be discussed briefly. This summary, and the following detailed description, will provide an understanding of the present embodiments and the advantages they exhibit, including, without limitation, increased protection for the user, better visibility in a low-light environment, and a reduction or elimination of medicament residue on an outer surface of a sealing stopper in the medicament vial.

One embodiment of the present cap adapter comprises a transverse wall portion with a first lumen passing through it. A vial-engaging portion of the cap adapter includes a plurality of clamping members that are circumferentially spaced about an edge of the transverse wall portion and that extend distally from the transverse wall portion. The clamping members are configured to snap fit about a mouth portion of the vial to secure the cap adapter to the vial. A spike extends distally from the transverse wall portion and defines a second lumen passing through the transverse wall portion. The second lumen is spaced from and not in fluid communication with the first lumen. The spike includes a sharp distal tip that is configured to pierce a sealing stopper on the vial. A cone-shaped shield element extends proximally from a vertex defining an inlet port that communicates with the first lumen, the shield element flaring radially outwardly from the inlet port. The shield element is configured to guide a hypodermic needle toward the first lumen, thereby reducing the risk of needlestick to a user handling the vial.

Another embodiment of the present cap adapter comprises a transverse wall portion with a first lumen passing through it. A vial-engaging portion of the cap adapter includes a plurality of clamping members that are circumferentially spaced about an edge of the transverse wall portion and that extend distally from the transverse wall portion. The clamping members are configured to snap fit about a mouth portion of the vial to secure the cap adapter to the vial. A light source cooperates with the cap adapter and is configured to illuminate at least a portion of the cap adapter to enhance the visibility of the vial in a low-light environment.

Another embodiment of the present cap adapter comprises a transverse wall portion with a first lumen passing through it. A vial-engaging portion of the cap adapter includes a plurality of clamping members that are circumferentially spaced about an edge of the transverse wall portion and that extend distally from the transverse wall portion. The clamping members are configured to snap fit about a mouth portion of the vial to secure the cap adapter to the vial. A secondary sealing member abuts a distal face of the transverse wall portion and seals a distal end of the first lumen.

BRIEF DESCRIPTION OF THE DRAWINGS

The various embodiments of the present cap adapters and associated methods now will be discussed in detail with an emphasis on highlighting the advantageous features. These embodiments depict the novel and non-obvious cap adapters shown in the accompanying drawings, which are for illustrative purposes only. These drawings include the following figures, in which like numerals indicate like parts.

DETAILED DESCRIPTION

Figure 1:
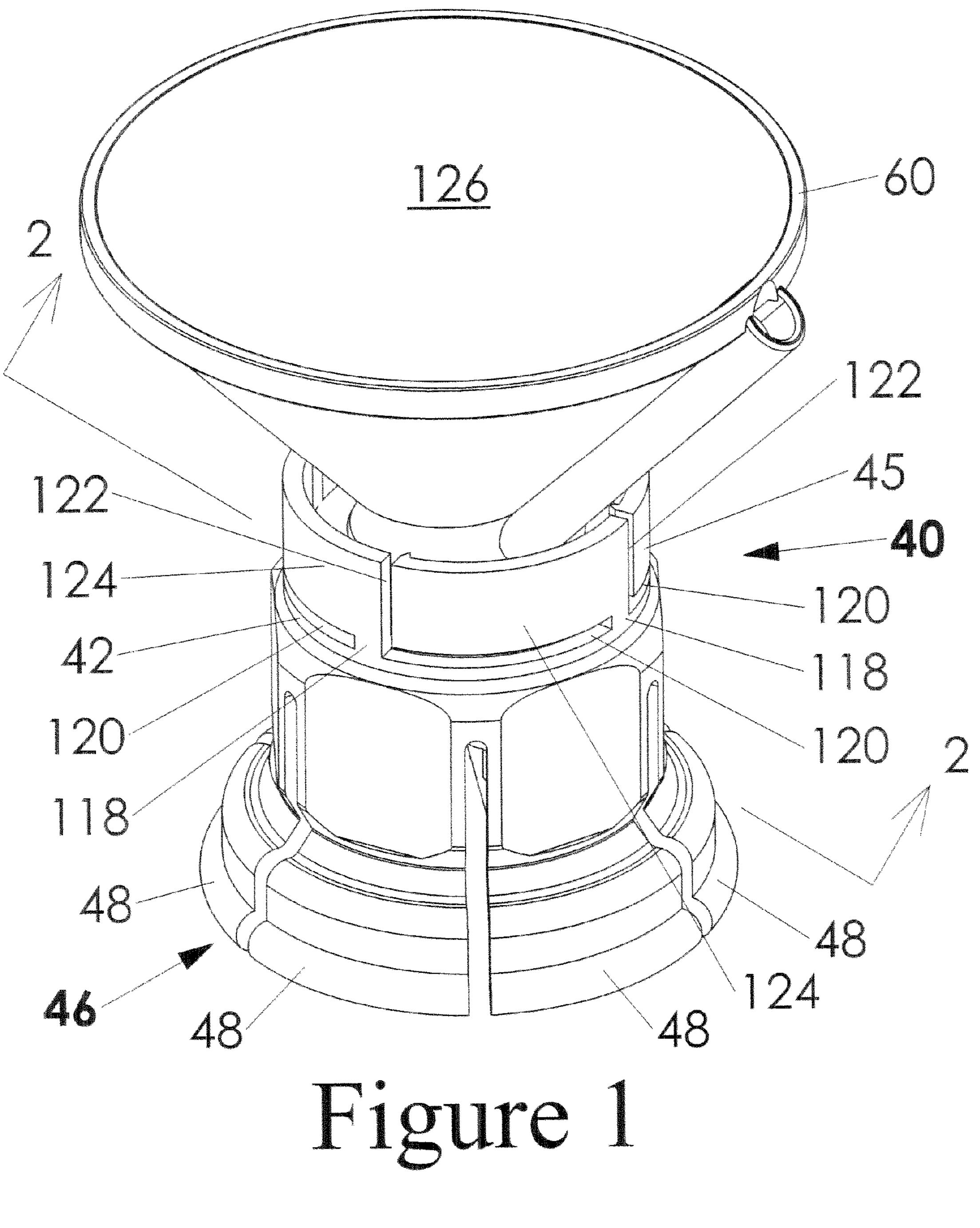
FIG. 1 is a perspective view of one embodiment of a cap adapter for a medicament vial in accordance with the present disclosure.

The following detailed description describes the present embodiments with reference to the drawings. In the drawings, reference numbers label elements of the present embodiments. These reference numbers are reproduced below in connection with the discussion of the corresponding drawing features. As used in the description below, the terms "proximal" and "proximally" denote a direction toward the user, while the terms "distal" and "distally denote a direction away from the user.

Figure 2A:
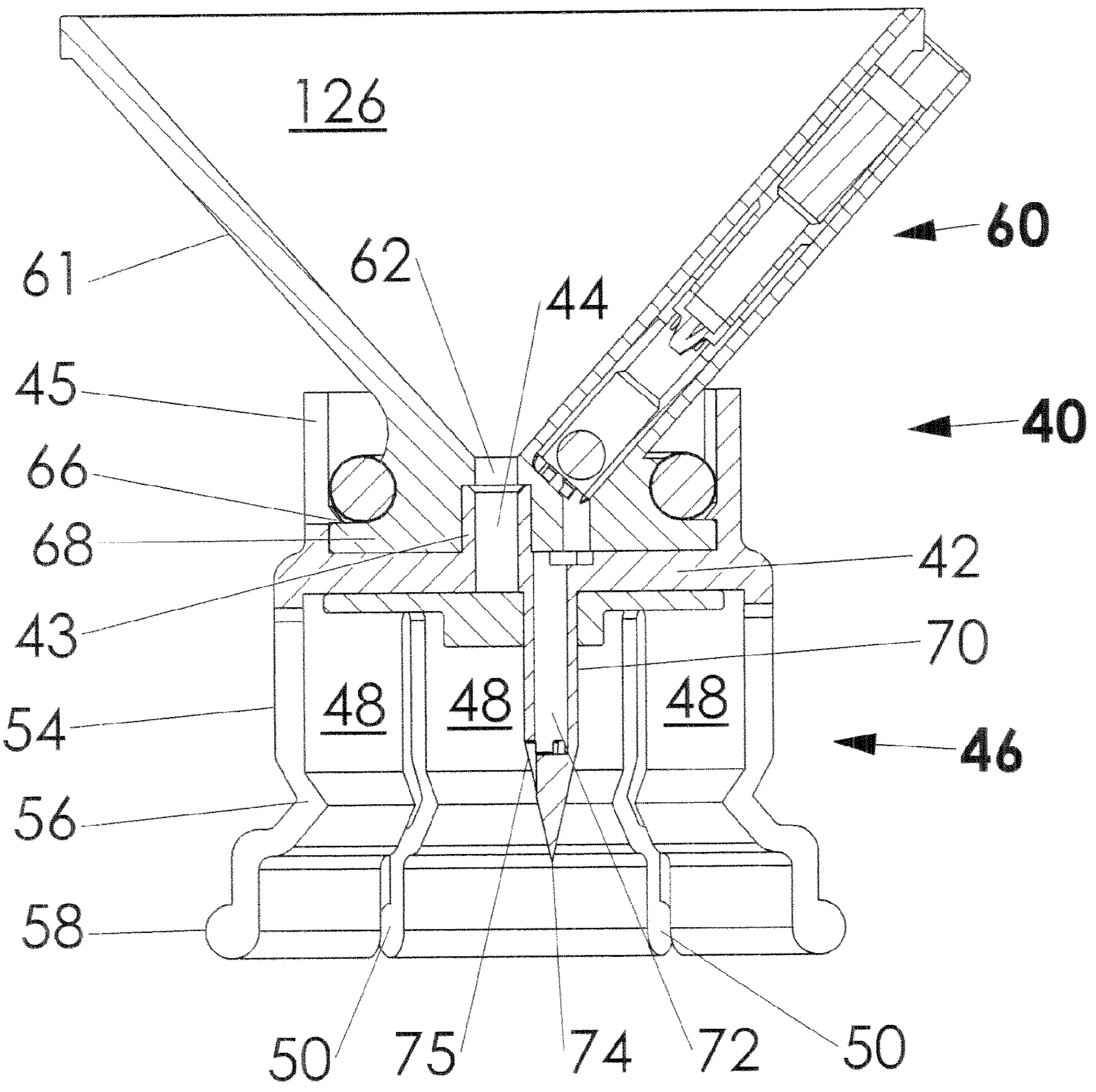
FIGS. 2A and 2B are cross-sectional views of the cap adapter of FIG. 1, taken through the line 2-2 in FIG. 1.
Figure 2B:
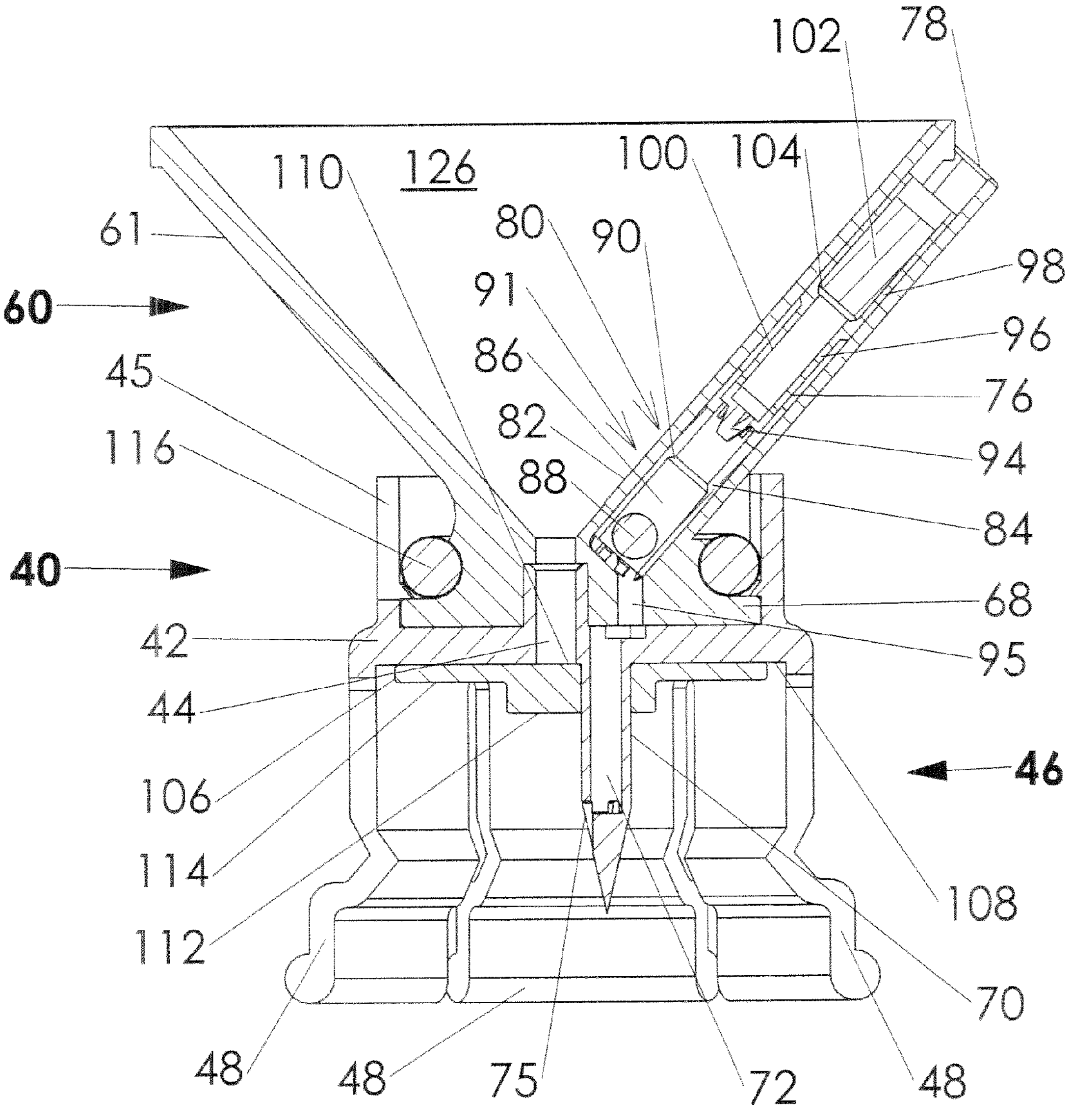
Figure 3:
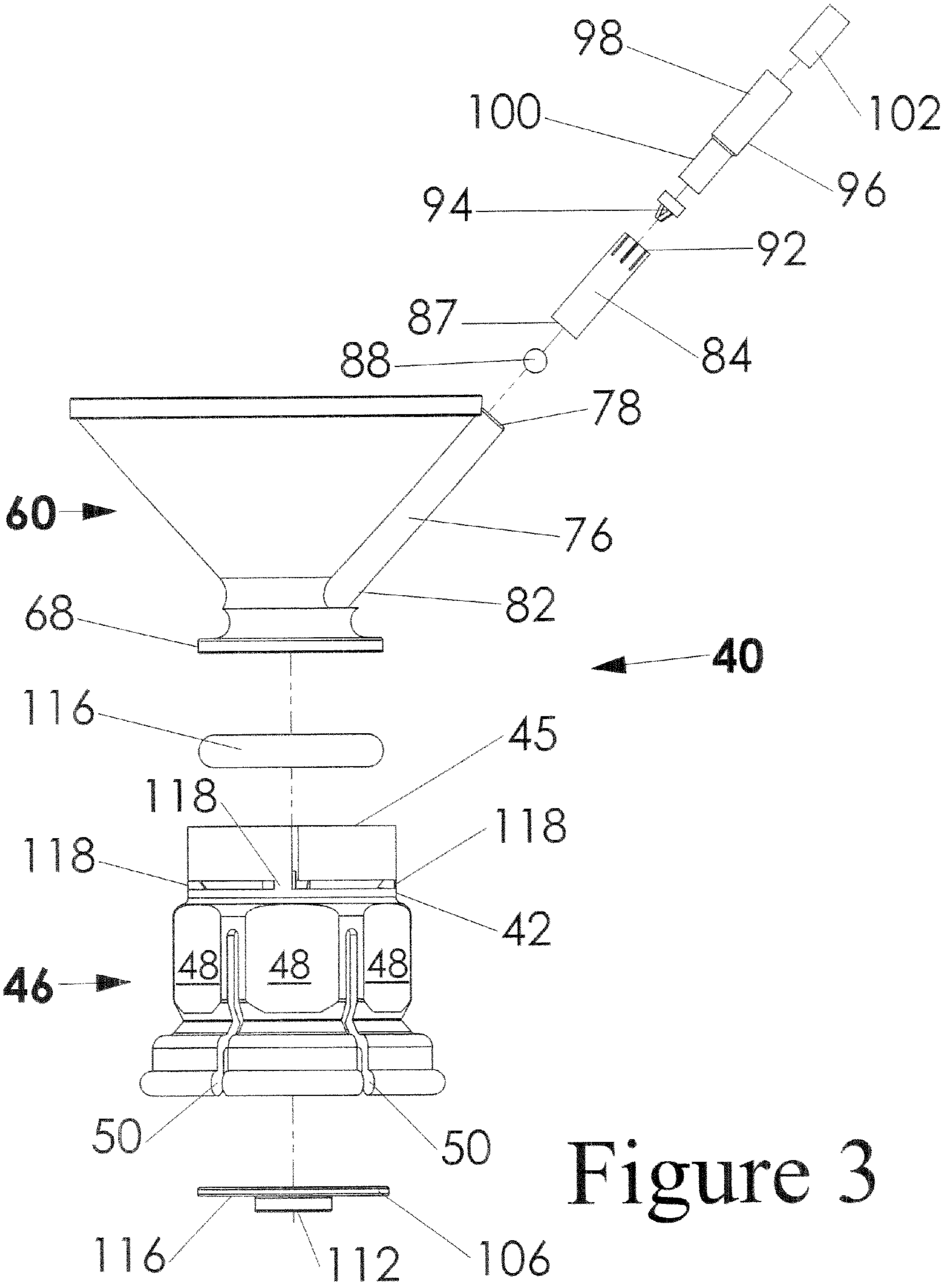
FIG. 3 is an exploded front elevation view of the cap adapter of FIG. 1.

FIGS. 1-3 illustrate one embodiment of the present cap adapter 40 for a medicament vial. (FIGS. 2A and 2B are identical to provide sufficient space to show clearly, and without clutter, the numerous reference numbers and lead lines needed to describe the structure illustrated therein.) The cap adapter 40 is configured to facilitate the transfer of liquid medicament from the vial into a syringe, as described in further detail below. With reference to FIG. 2A, the cap adapter 40 comprises a transverse internal wall portion 42. Art integral conduit portion 43 extends proximally from the transverse internal wall portion 42 and defines a first lumen 44 that passes through the transverse wall portion 42. The first lumen 44 is located and configured to permit passage of a hypodermic syringe needle during a transfer of liquid medicament from the vial and into the syringe, as explained below. A circumferential axial wall portion 45 extends proximally from a peripheral edge of the transverse wall portion 42.

A vial-engaging portion 46 of the cap adapter 40 comprises a plurality of clamping members 48 that extend distally and substantially axially from an outer peripheral edge of the transverse wall portion 42. The clamping members 48 are circumferentially separated from each other by a plurality of substantially axial slots 50. Each clamping member 48 is cantilevered radially from the wall portion 42. In cross-section (FIG. 2A), each clamping member 48 includes a substantially straight portion 54 extending distally from the wall portion 42, an internally ridged portion 56 and a radially outwardly flaring skirt portion 58. The clamping members 48 are configured to snap fit about a mouth portion of a standard medicament vial to secure the cap adapter 40 to the vial, as described below.

A shield element 60 extends proximally from the transverse wall portion 42. In the illustrated embodiment, the shield element 60 includes a substantially conical entrance portion 61 (FIGS. 2A and 2B) extending proximally from an annular base 68 that is circumferentially surrounded by the axial wall portion 45, and that has a distal surface that seats against the proximal surface of the transverse wall portion 42. The conical configuration of the entrance portion 61 of the shield element 60 serves to guide a syringe needle toward the first lumen 44, thereby to reduce a risk of needlestick to a user handling the vial, as described in further detail below.

As shown, in FIGS. 2A and 2B, at the vertex of the conical entrance portion 61 is an inlet port 62 that is in fluid communication with the first, lumen 44. The conical entrance portion 61 flares radially outwardly from, the inlet port 62. In the illustrated embodiment, the shield element 60 is fabricated as a separate piece from the wall portion 42, but it may be integral therewith or adhesively fixed thereto. If, as shown, the shield element 60 and the transverse wall portion 42 are separate components, the shield element 60 may advantageously be held in place against the transverse wall, portion 42 by a circumferential lip or detent 66 that extends radially inwardly over the peripheral edge of the base 68.

A hollow spike 70 extends distally from the distal surface of the transverse wall portion 42. The interior of the spike 70 defines a second lumen 72, the proximal portion of which passes through the transverse wall portion 42. The second lumen 72 is spaced from, and fluidly isolated from, the first lumen 44. The spike 70 includes a sharp tip 74 at its distal end that is configured to pierce a sealing stopper 138 (FIG. 4) in the mouth portion of the vial, as described below. Just proximal of the tip 74 is a radial outlet port 75 that communicates with the second lumen 72. As described in further detail below, the spike 70 establishes fluid communication between the ambient atmosphere and the interior of the vial. Ambient air can thus pass into the vial to equalize the fluid pressure on either side of the sealing stopper 138 as medicament is withdrawn from the vial.

The cap adapter 40 further includes a vent passage 76 in fluid communication with the second lumen 72 by means of an axial connecting passage 95 that extends through the base 68 of the shield element 60 between a distal end 82 of the vent passage 76 and a proximal end of the second lumen 72. The vent passage 76 is open to the ambient atmosphere at a proximal end 78 spaced from the second lumen 72. The vent passage 76 includes a one-way valve or check valve 80 configured to allow air to flow into the vial through the vent passage 76 and the second lumen 72. The one-way valve 80 is further configured to inhibit the liquid medicament in the vial from escaping through the second lumen 72 and the vent passage 76.

In the illustrated embodiment, the vent passage 76 extends along an outside of the conical entrance portion 61 of the shield 60. However, those of ordinary skill in the art will appreciate that in other embodiments the vent passage 76 could be located elsewhere. With reference to FIGS. 2B and 3, the distal end 82 of the vent passage 76 receives an overflow riser 84. The overflow riser 84 is substantially cylindrical and includes a space 86 at a distal end 87 (FIG. 3) for receiving a ball 88 (FIGS. 2B and 3) having a diameter that is slightly smaller than an interior diameter of the space 86 so that air can flow past the ball, as discussed below.

An intermediate portion of the overflow riser 84 includes a step 90 (FIG. 2B) at which the interior diameter of the overflow riser 84 decreases. The diameter of the step 90 is smaller than that of the ball 88 so that the ball 88 creates a seal inside the overflow riser 84 when it rests against the step 90, as when the cap adapter 40 is inverted from the orientation shown in FIG. 2B. In the inverted orientation, engagement of the ball 88 against the step 90 substantially prevents liquid medicament from escaping to ambient through the vent passage 76. Thus, the ball 88 and the overflow riser 84 together comprise a ball valve 91 (FIG. 2B) that allows flow in only one direction, from the ambient atmosphere into the vial. The operation of the ball valve 91 is discussed in greater detail below.

As best shown, for example, in FIGS. 2B and 3, the overflow riser 84 has a proximal end 92 that receives a duckbill valve 94. The duckbill valve 94, the structure of which is well-known to those of skill in the art, is oriented so that it allows fluid flow in only one direction (i.e., distally), through the vent passage 76, from the ambient atmosphere into the vial. Like the ball valve 91, the duckbill valve 94 inhibits the passage of the liquid medicament from the vial to the ambient environment through the vent passage 76. Thus, together the ball valve 91 and the duckbill valve 94 provide redundant seals that greatly reduce the likelihood that any medicament will leak out of the vial and the cap adapter through the vent passage 76. The interior space 86 of the overflow riser 84 provides a chamber for receiving and capturing any proximal backflow of medicament through the second lumen 72 and the internal axial passage 95. The slightly smaller diameter of the ball 88 as compared to the ball receiving space 86 enables any medicament that enters the overflow riser 84 to travel back down into the vial when the vial is held right-side up (i.e., the orientation shown in FIGS. 2A and 2B).

The vent passage 76 advantageously enables air to flow from the ambient atmosphere into the vial to equalize the pressure on either side of the sealing stopper 138 and, to facilitate withdrawal of medicament from the vial, as discussed in further detail below. From the ambient atmosphere, air flows into the vent passage 76, through the duckbill valve 94 and into the overflow riser 84. Properties of the duckbill valve 94 can be tailored to produce a desired cracking pressure at which the duckbill valve 94 opens to allow airflow therethrough. The air then, flows through the overflow riser 84 and past the ball 88. Even if the cap adapter 40 is inverted so that the ball 88 rests against the step 90, air may flow past the ball 88 if a pressure differential across the ball 88 is greater than a cracking pressure to cause the ball 88 to momentarily lose sealing contact with the step 90. Properties of the ball 88 can be tailored to produce a desired cracking pressure. Once past the step 90, air may flow around the ball 88, since it is smaller in diameter than the internal diameter of the space 86 in the overflow riser 84. The air then passes into and through the axial internal passage 95, into and through the second lumen 72, and then through the radial outlet port 75 and into the vial.

The vent passage 76 may include in its interior an optional tubular filter seat 96 upstream from (i.e., proximally from) the duckbill valve 94. If present, the filter seat 96 advantageously has a distal portion 100, having a first outside diameter, that is received in the proximal end of the overflow riser 84, and to which the upstream (proximal) end of the duckbill valve 94 is fixed for fluid communication therewith. The filter seat 96 has a proximal portion 98, with a second outside diameter larger than the first outside diameter of the distal portion 100, that receives an optional filter 102. The filter 102 removes contaminants and pathogens from ambient air passing through the vent passage 76. The filter 102 may optionally be treated with an anti-microbial substance, of a type well-known in the art. The filter 102 seats against a shoulder 104 (FIG. 2B) formed at the junction of the distal portion 100 and the proximal portion 98 to prevent the filter 102 from being sucked down toward the overflow riser 84 by inrushing air. The filter 102 may be replaceable, either separately from, or together with, the filter seat 96.

With continued reference to FIGS. 2B and 3, a secondary sealing member 106 may optionally be provided on the distal, surface 108 of the transverse wall portion 42 so as to seal a distal end 110 of the first lumen 44. The secondary sealing member 106 is formed of an elastomeric material, and it is located, and configured to seat against the exterior surface of the sealing stopper 138 on the vial when the cap adapter 40 is secured about the mouth portion of the vial, as discussed in further detail below. In the illustrated embodiment, the secondary sealing member 106 is shaped substantially as a stepped disk, including a thickened central portion 112 circumferentially surrounded by a thinner portion 114. The central portion 112 seals the distal end 110 of the first lumen 44. It will be appreciated that the secondary sealing member 106 may have other configurations, such as a constant thickness, a smaller diameter, etc.

With continued reference to FIGS. 2B and 3, the illustrated cap adapter 40 may further comprise an optional, light source 116 configured to illuminate at least a portion of the cap adapter 40. In the illustrated embodiment, the light source 116 comprises a chemiluminescent ring 116 that extends around the base portion 68 of the shield 60, substantially surrounding the first lumen 44. The circumferential axial wall portion 45 extends proximally from the edge 52 of the wall portion 42 and surrounds the light source 116.

With reference to FIGS. 1 and 3, the axial wall portion 45 connects to the transverse wall portion 42 at a plurality of discrete locations 118, creating a plurality of first gaps 120 that separate the axial wall portion 45 from the transverse wail portion 42. A plurality of second gaps 122 extend perpendicularly to the plurality of first gaps 120 and separate sections 124 of the axial wall portion 45 from one another. The gaps 120, 122 allow the sections 124 to readily flex inwardly under a radial squeezing force provided around the periphery of the axial wall portion 45. A user can, for example, provide a squeezing force by wrapping his or her thumb and forefinger around the axial wail portion 45. The squeezing force causes the sections 124 to bear against the light source 116. A threshold squeezing force induces a chemical reaction within the chemiluminescent ring 116 that produces light.

In certain embodiments, the cap adapter 40 is constructed of one or more translucent materials. For example, the cap adapter 40 may be constructed of polycarbonate, acrylic, polypropylene, styrene, or any other suitable plastic material. When the light source 116 is illuminated, light is transmitted through the cap adapter to provide an advantageous visual cue to a user at night or in a low ambient light environment. Thus, the user may reliably guide a syringe needle into the first lumen 44 when there is little or no ambient light, further reducing the risk of needlestick to the user.

In certain embodiments, portions of the cap adapter 40 may be constructed from opaque materials, or treated to reduce or eliminate the ability to transmit light. For example, on a darkened, battlefield it may be advantageous to reduce the visibility of the cap adapter 40 to others besides the user. Thus, in certain embodiments, substantially all portions of the cap adapter 40 other than the interior 126 (FIGS. 1, 2A and 2B) of the shield 60 may be constructed of or treated with an opaque or semi-opaque material. To the user looking into the interior 126 of the shield 60 from the proximal side, the shield 60 will appear to glow and thus guide the user to the first lumen 44.

Figure 4:
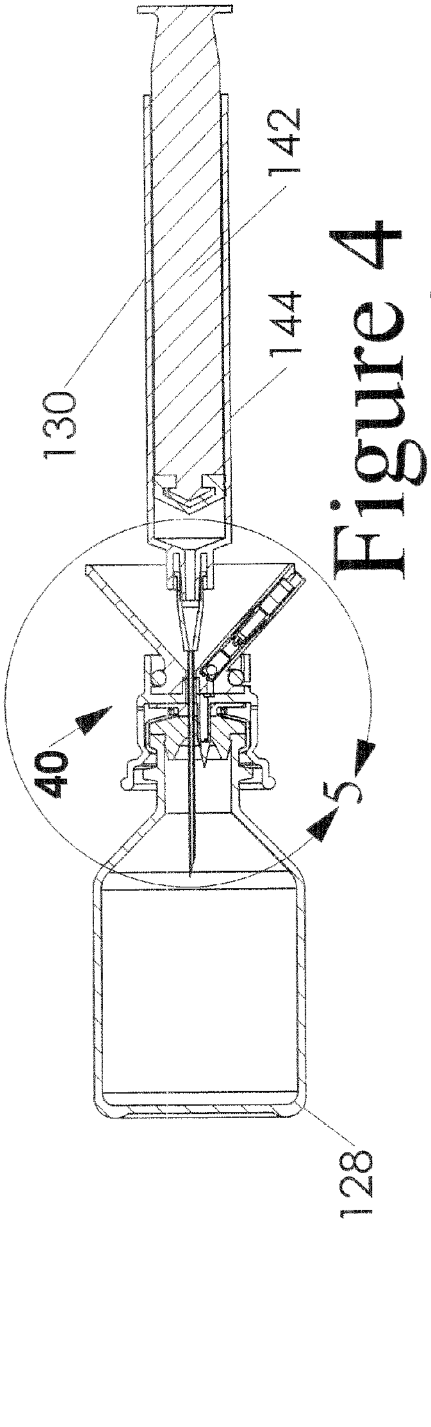
FIG. 4 is a cross-sectional view of the cap adapter of FIGS. 1-3 in combination with a medicament vial and a syringe.
Figure 5:
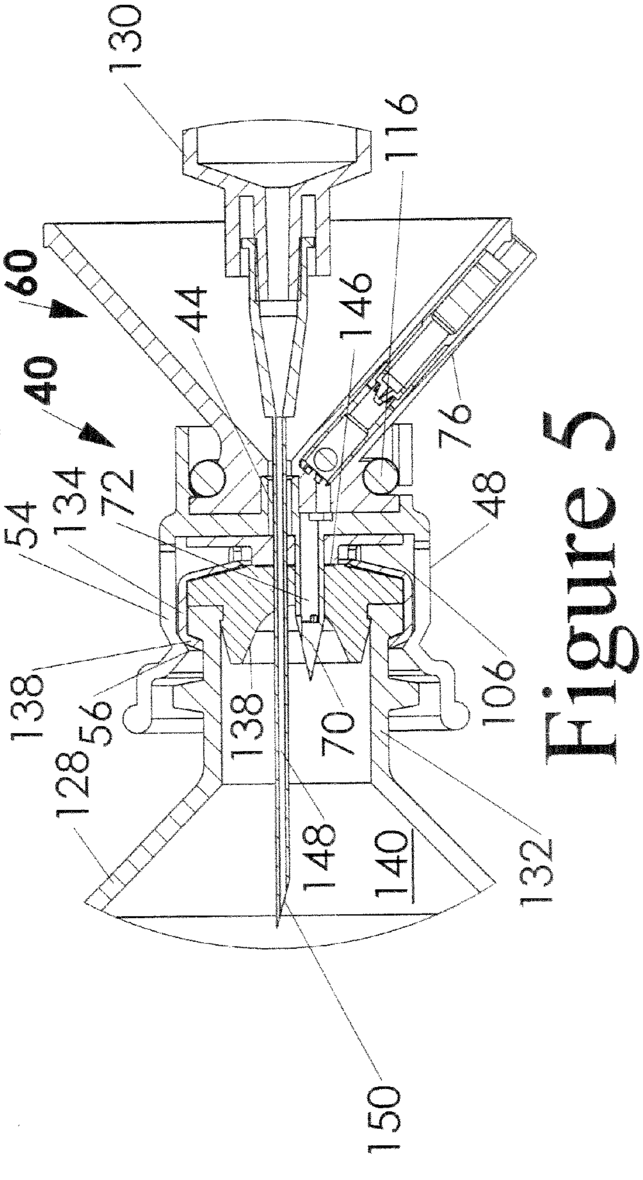
FIG. 5 is a detail view of the portion of FIG. 4 indicated by the circle 5-5.

FIG. 4 illustrates the cap adapter 40 of FIGS. 1-3 engaging a medicament vial 128 and a syringe 130. FIG. 5 illustrates a detail view of the portion of FIG. 4 indicated by the circle 5-5. With reference to FIG. 5, the clamping members 48 extend around the mouth portion 132 of the vial 128. The straight portion 54 of each clamping member 48 extends along a flat side of an enlarged portion 134 of the mouth portion 132. The straight portions 54 may abut the enlarged mouth portion 134 to reduce relative lateral movement of the vial 128 and the cap adapter 40. The internally-ridged portion 56 extends around an underside 136 of the enlarged mouth portion 134 to resist relative axial movement of the cap adapter 40 away from the vial 128. Since the clamping members 48 are flexible, however, and since they are separated from one another by the gaps 50 (FIGS. 2A and 3), the cap adapter 40 may be removed from the vial 128 by applying sufficient oppositely directed axial forces to the vial 128 and the cap adapter 40.

With continued reference to FIG. 5, the spike 70 penetrates the sealing stopper 138 and establishes fluid communication between the interior 140 of the vial 128 and the vent passage 76 via the second lumen 72 and the axial passage 95. The spike 70 thus enables ambient air to enter the vial 128 as medicament is withdrawal. The entering air equalizes fluid pressures on opposite sides of the sealing stopper 138, making it easier for the user to withdraw liquid from the vial 128 since he or she does not have to overcome a vacuum force tending to pull the syringe plunger 142 (FIG. 4) back into the syringe barrel 144. As discussed above, in certain embodiments the filter 102 advantageously reduces the likelihood of contaminants entering the vial with the incoming ambient air 128. Further, the valves 91, 94 reduce the likelihood that the medicament within the vial 128 will escape to the ambient.

With continued reference to FIG. 5, the secondary sealing member 106 abuts against the exterior surface 146 of the vial sealing stopper 138. A syringe needle 148 extends through the first lumen 44, penetrates the secondary sealing member 106 and the sealing stopper 138, and extends into the vial interior 140. The user may withdraw medicament from the vial 128 by positioning the distal tip 150 of the needle 148 within the liquid and drawing back on the plunger 142. The user may then withdraw the needle 148 from vial 128 to perform an injection.

Figure 6:
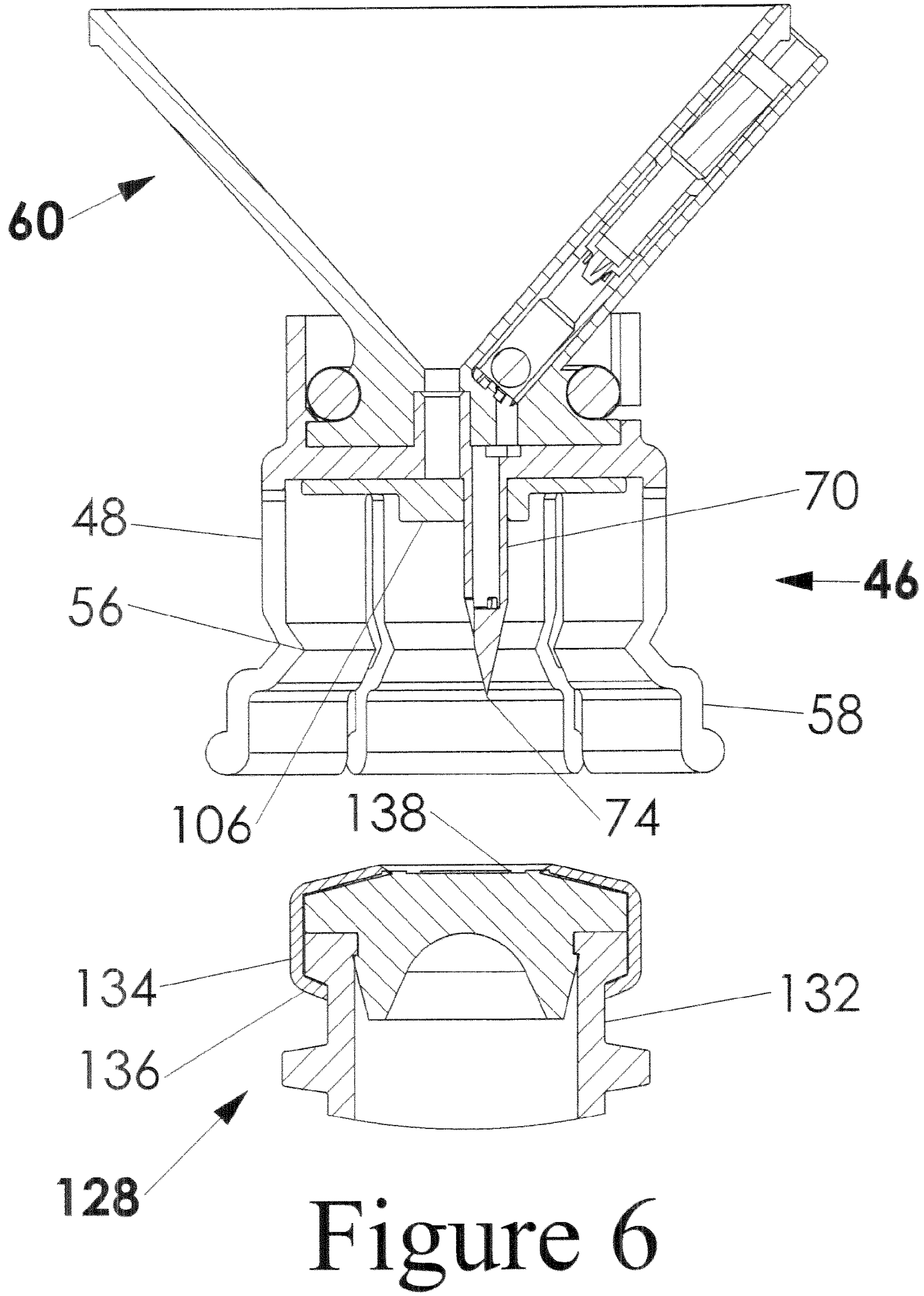
FIG. 6 is an exploded cross-sectional view of the cap adapter of FIGS. 1-3 in combination with a medicament vial.
Figure 7:
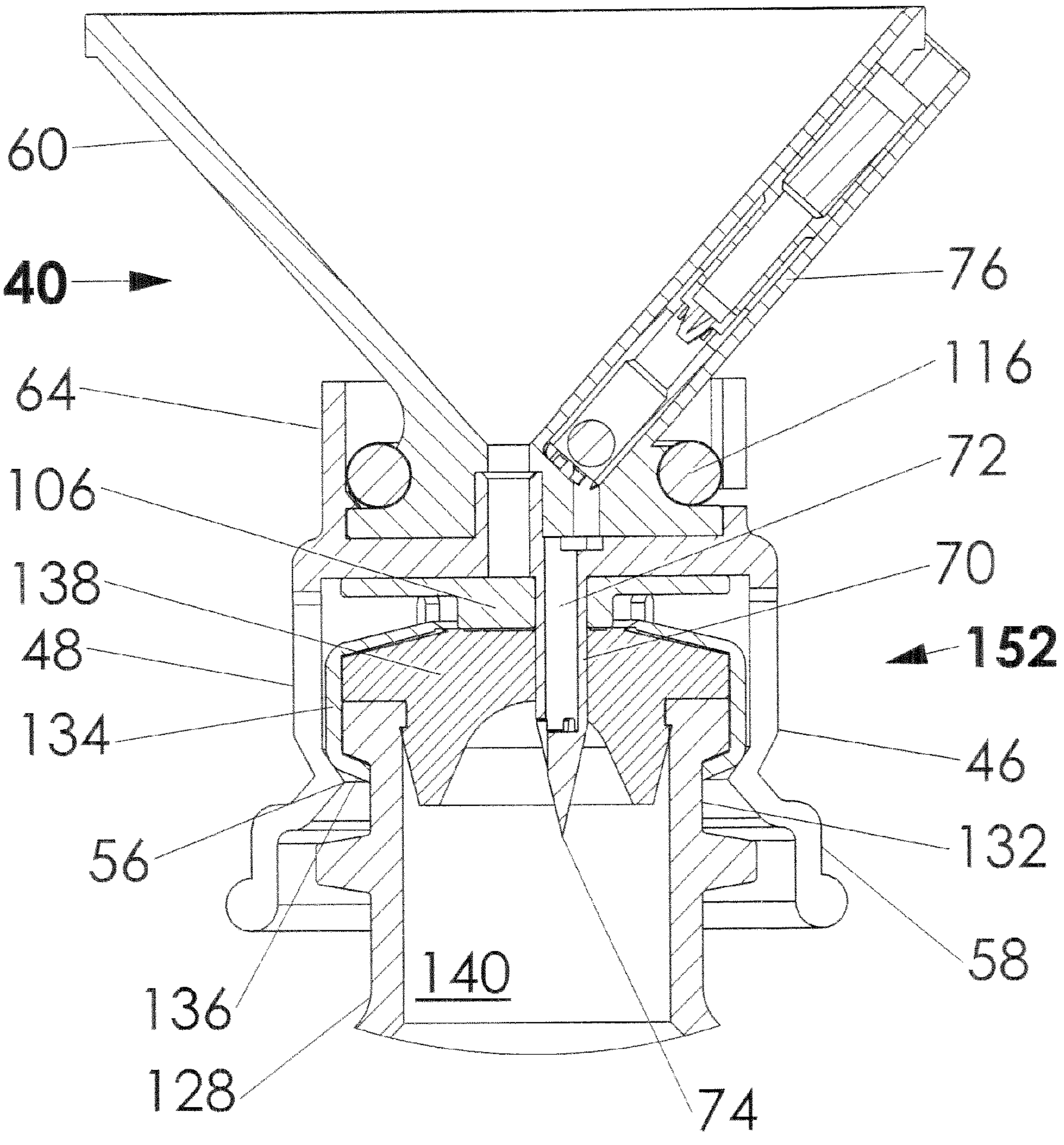
FIG. 7 is a cross-sectional view of the assembled cap adapter and medicament vial of FIG. 6.

FIGS. 4-7 illustrate one embodiment of a method of using the present cap adapter 40 to withdraw medicament from a vial 128. With reference to FIG. 6, the user positions the vial-engaging portion 46 adjacent the mouth portion 132 of the vial 128 with the skirt portion 58 facing the enlarged portion 134. The user then applies digital pressure to force the vial 128 and the cap adapter 40 together. With reference to FIGS. 6 and 7, as the vial 128 and the cap adapter 40 come together, the sharp tip 74 of the spike 70 penetrates the sealing stopper 138. The clamping members 48 expand radially as the ridge portion 56 passes over the enlarged portion 134. When the ridge portion 56 reaches the underside 136 of the mouth portion 132, the vial-engaging portion 46 snaps onto the vial 128 as shown in FIG. 7 to create a vial/cap assembly 152. In the vial/cap assembly 152, the secondary sealing member 106 abuts against the exterior (proximal) surface of the sealing stopper 138, and the spike 70 establishes fluid communication between the interior 140 of the vial 128 and the vent passage 76, as described above.

The user then grasps the vial/cap assembly 152, for example, by wrapping his or her thumb and forefinger around the cap adapter 40 in the region of the axial wall portion 45 and/or the region of the vial-engaging portion 46. In this configuration, most if not all, of the user's hand and fingers are positioned behind the conical entrance portion 61 of the shield element 60. If the user requires additional light, such as in a low ambient light environment, the user squeezes the axial wall portion 45 to activate the chemiluminescent ring 116.

With reference to FIG. 5, using the shield element 60, and, if necessary, the light source 116, the user guides the needle 148 into the first lumen 44. The entrance portion 61 of the shield 60 advantageously guides the distal tip 150 of the needle 148 toward the first lumen 44 while at the same time forming a barrier between the sharp needle tip 150 and the user's hand and fingers. The user is thus well protected from accidental needlestick. The shield element 60 may be constructed of any suitable material that substantially prevents the needle from piercing the shield 60 under conditions of anticipated use. The user is thus unlikely to be stuck by a needle passing completely through the shield 60 and into the user's hand.

Guiding the needle into the first lumen 44, the user pierces the secondary sealing member 106 and the sealing stopper 138 to insert the needle tip 150 into the vial 128 as shown in FIGS. 4 and 5. The user then withdraws a desired amount of medicament from the vial 128 by positioning the distal tip 150 of the needle 148 within the liquid and drawing back on the plunger 142. The user then withdraws the needle 148 from the vial 128 through the sealing stopper 138 and the secondary sealing member 106. Advantageously, the abutment of the secondary sealing member 106 and the sealing stopper 138 creates a fluid seal that prevents the liquid medicament from being deposited on the outer surface 146 of the sealing stopper 138 through the tip 150 of the needle 148 as it passes the sealing stopper 138. The abutment thus reduces the likelihood that medicament residue will be left on the exterior surface 146 of the sealing stopper 138, which could result in contamination of the environment by such residue.

It will be appreciated that the shield element 60 could have a shape different from the illustrated embodiments in which it is substantially cone-shaped. For example, the shield 60 could include an outwardly flared portion in the region near the wall portion 42 and a substantially cylindrical portion adjoining the flared portion at a location spaced proximally from the wall portion 42. Substantially any shape that guides the needle toward the first lumen 44 and/or protects the user from needlestick would be suitable.

Figure 14:
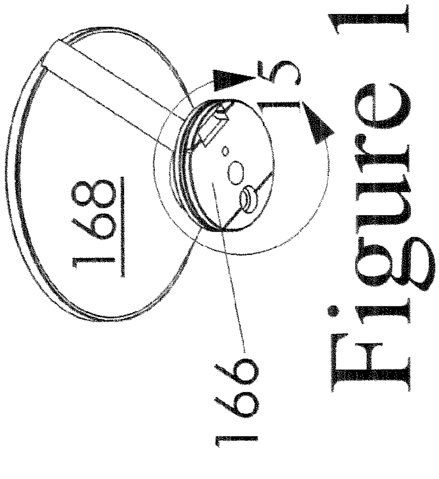
FIG. 14 is a bottom perspective view of the shield portion of the cap adapter of FIG. 8.
Figure 15:
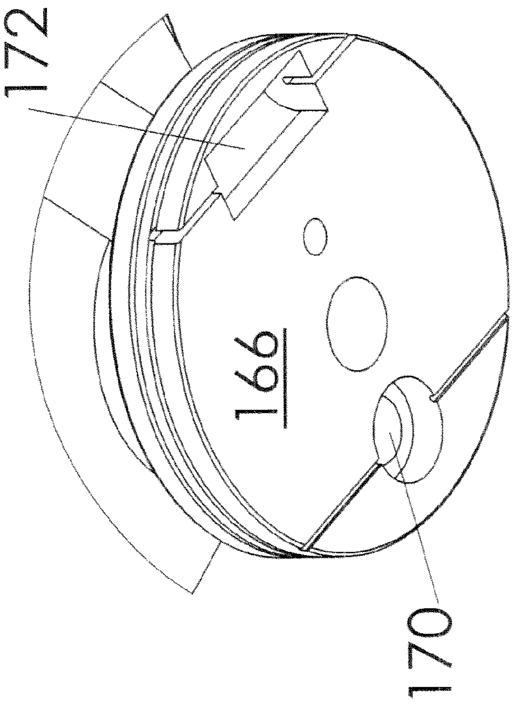
FIG. 15 is a detail view of the portion of FIG. 14 indicated by the circle 15-15.
Figure 13:
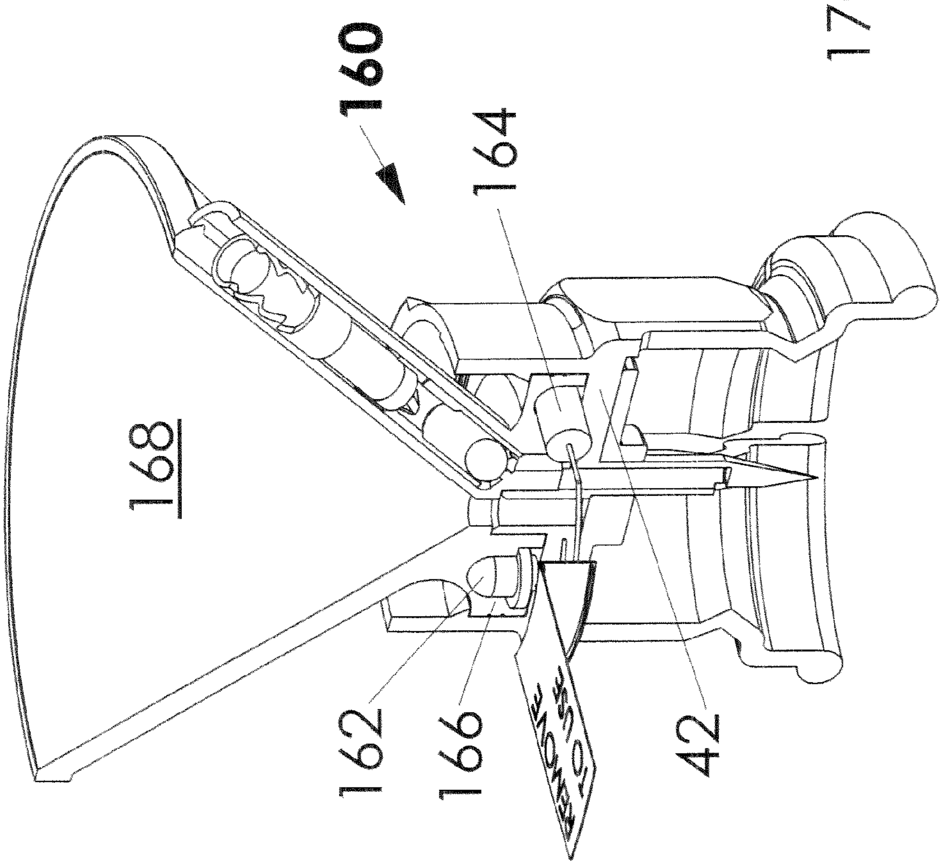
FIG. 13 is a sectioned perspective view of the cap adapter of FIG. 8, taken through the line 13-13 in FIG. 8.

FIGS. 8-19 illustrate another embodiment of the present cap adapter 160 for a medicament vial. The cap adapter 160 is similar in many respects to the cap adapter 40 described above and illustrated in FIGS. 1-7. The cap adapter 160, however, includes a light source 162 comprising a light-emitting diode (LED) 162 (FIGS. 10-13). A power source 164, such, as a battery 164, provides power to light the LED 162. With reference to FIGS. 9-13, the LED 162 and the battery 164 reside between the base 166 of the shield 168 and the wall portion 42. With reference to FIGS. 14 and 15, the shield base 166 includes cavities 170, 172 to accommodate the LED 162 and the battery 164, respectively.

Figure 12:
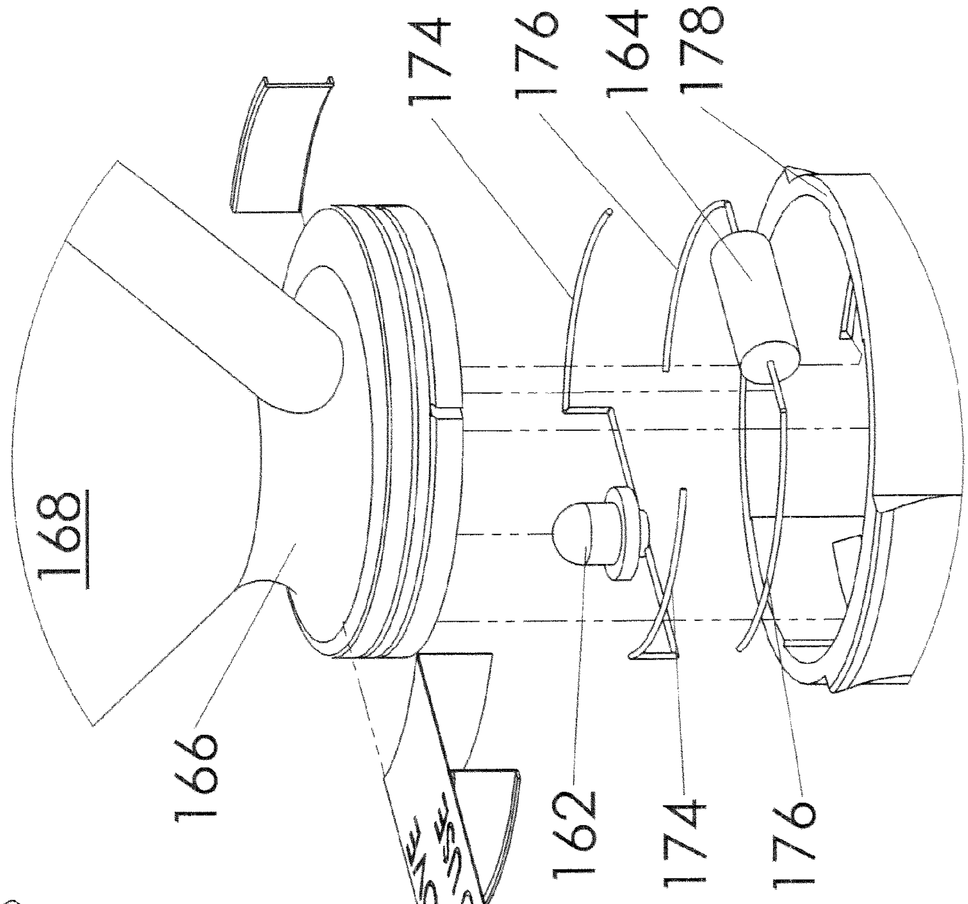
FIG. 12 is a detail view of the portion of FIG. 11 indicated by the circle 12-12.
Figure 11:
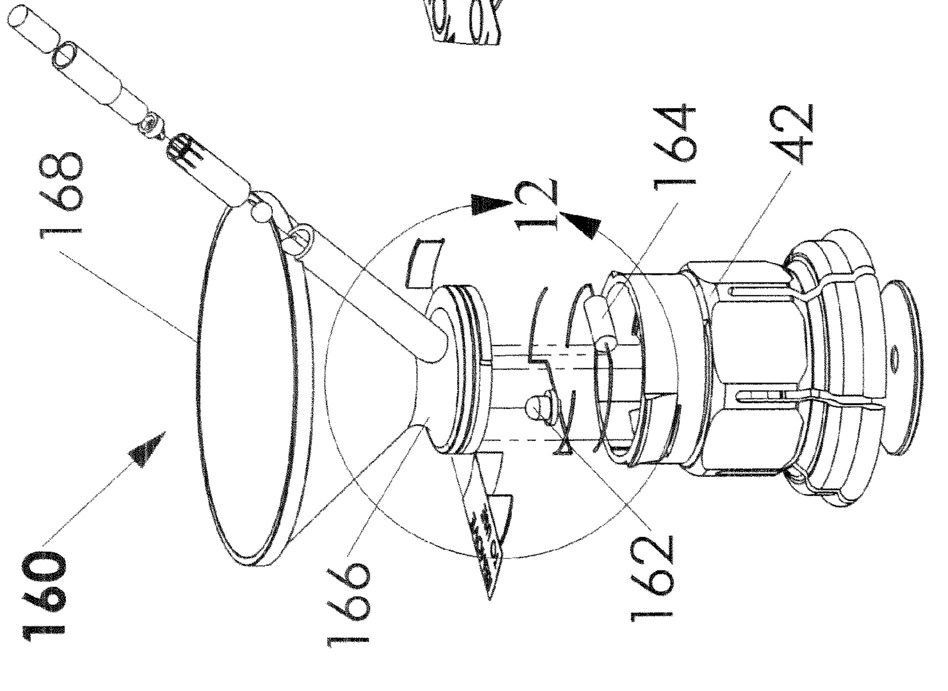
FIG. 11 is an exploded perspective view of the cap adapter of FIG. 8.

With reference to FIGS. 11 and 12, the LED 162 includes first electrical leads 174 extending in opposite directions from the LED 162, and the battery 164 includes second electrical leads 176 extending in opposite directions from the battery 164. The first and second electrical leads 174, 176 extend toward each other inside the curved interior of the axial wall portion 178. The first and second electrical leads 174, 176 overlap (FIG. 12), but do not contact each other (FIGS. 16-19). Thus, in an initial configuration no power flows from the battery 164 to the LED 162.

Figure 16:
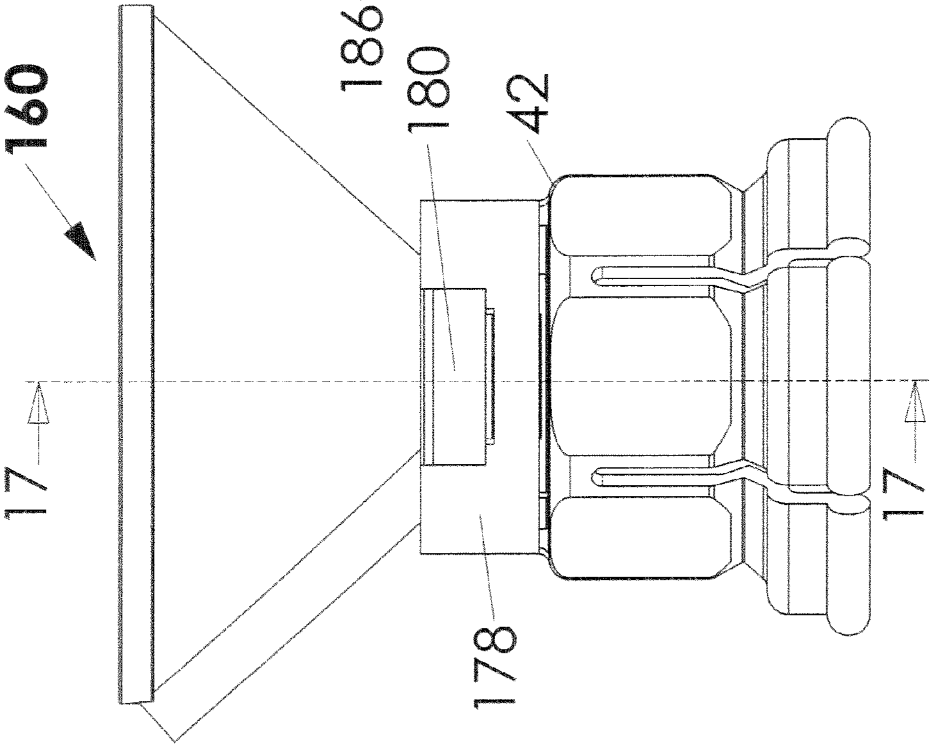
FIG. 16 is a rear elevation view of the cap adapter of FIG. 8.
Figure 17:
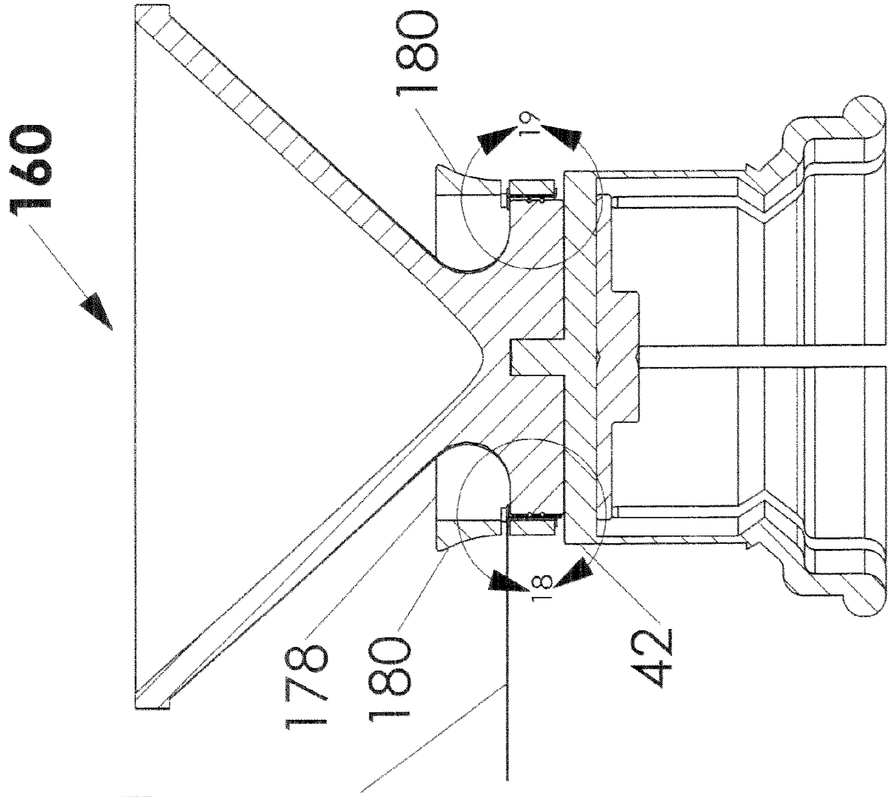
FIG. 17 is a cross-sectional view of the cap adapter of FIG. 16, taken through the line 17-17 in FIG. 16.
Figure 19:
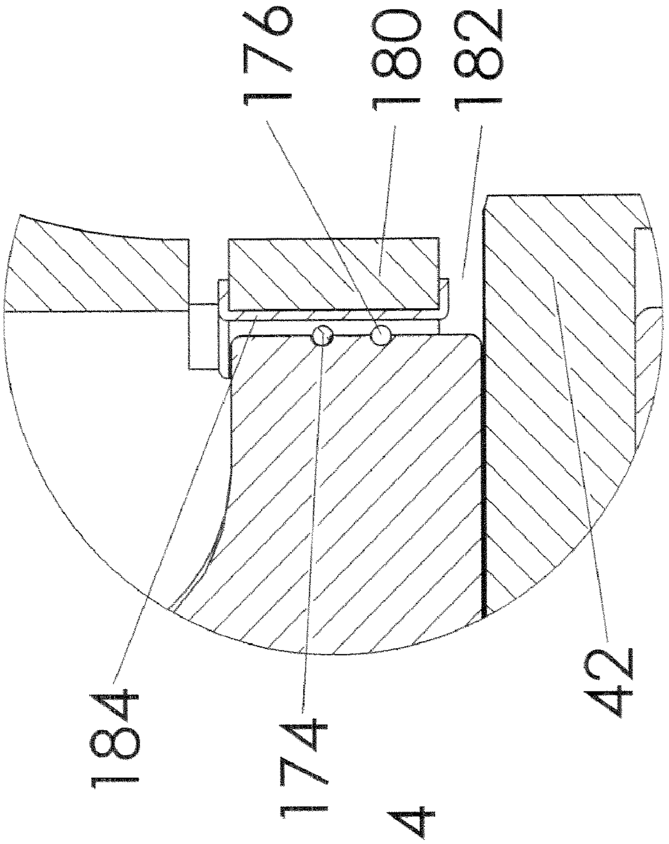
FIG. 19 is a detail view of the portion of FIG. 17 indicated by the circle 19-19.
Figure 18:
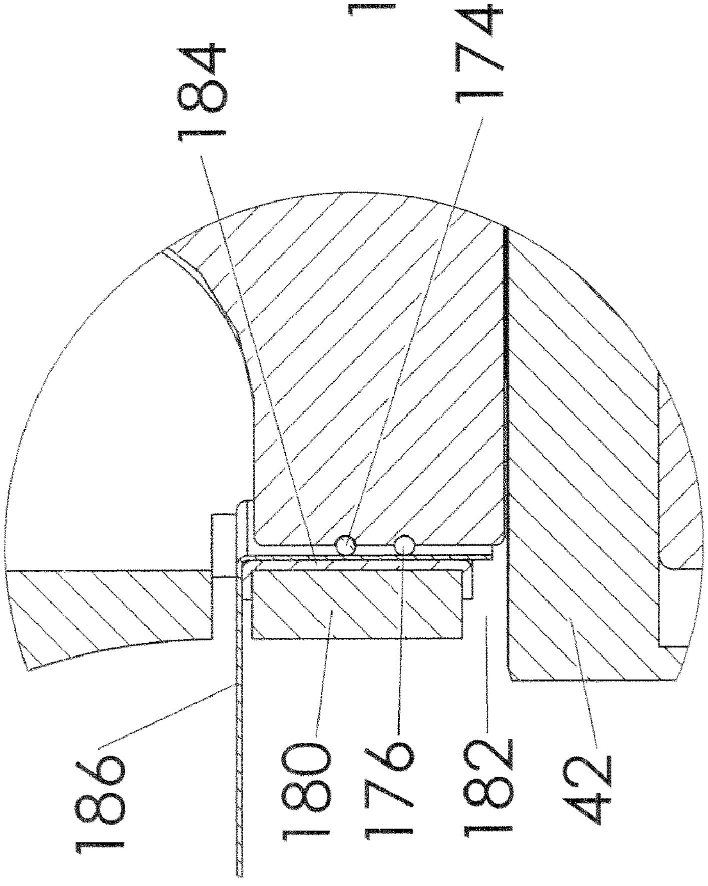
FIG. 18 is a detail view of the portion of FIG. 17 indicated by the circle 18-18.

With reference to FIGS. 16 and 17, the axial wall portion 178 includes first and second opposed tabs 180, which flare outwardly from the axial wall portion 178 at a position proximally spaced from the wall portion 42. The tabs 180 provide a contoured surface for the user's thumb and forefinger. With reference to FIGS. 18 and 19, gaps 182 space the tabs 180 from the wall portion 42 in the areas beneath the tabs 180. The gaps 182 facilitate the flexing of the axial wall portion 178 inwardly when the user squeezes the tabs 180. With reference to FIGS. 18 and 19, each of the tabs 180 includes a conductive layer 184 on its inward surface. Squeezing the tabs 180 brings the conductive layer 184 into contact with the first and second electrical leads 174, 176, completing the circuit that begins the flow of power from the battery 164 to the LED 162 and illuminates the LED 162. When the user releases the squeezing force on the tabs 180, the circuit is broken and the LED 162 darkens. The cap adapter 160 can thus advantageously be illuminated and darkened repeatedly. Not only does this feature prolong the lifespan of the cap adapter 160, but it also enhances the utility of the cap adapter 160 in environments where it is advantageous for the cap adapter 160 to be illuminated only intermittently for short periods of time, such as on a darkened battlefield.

Figure 8:
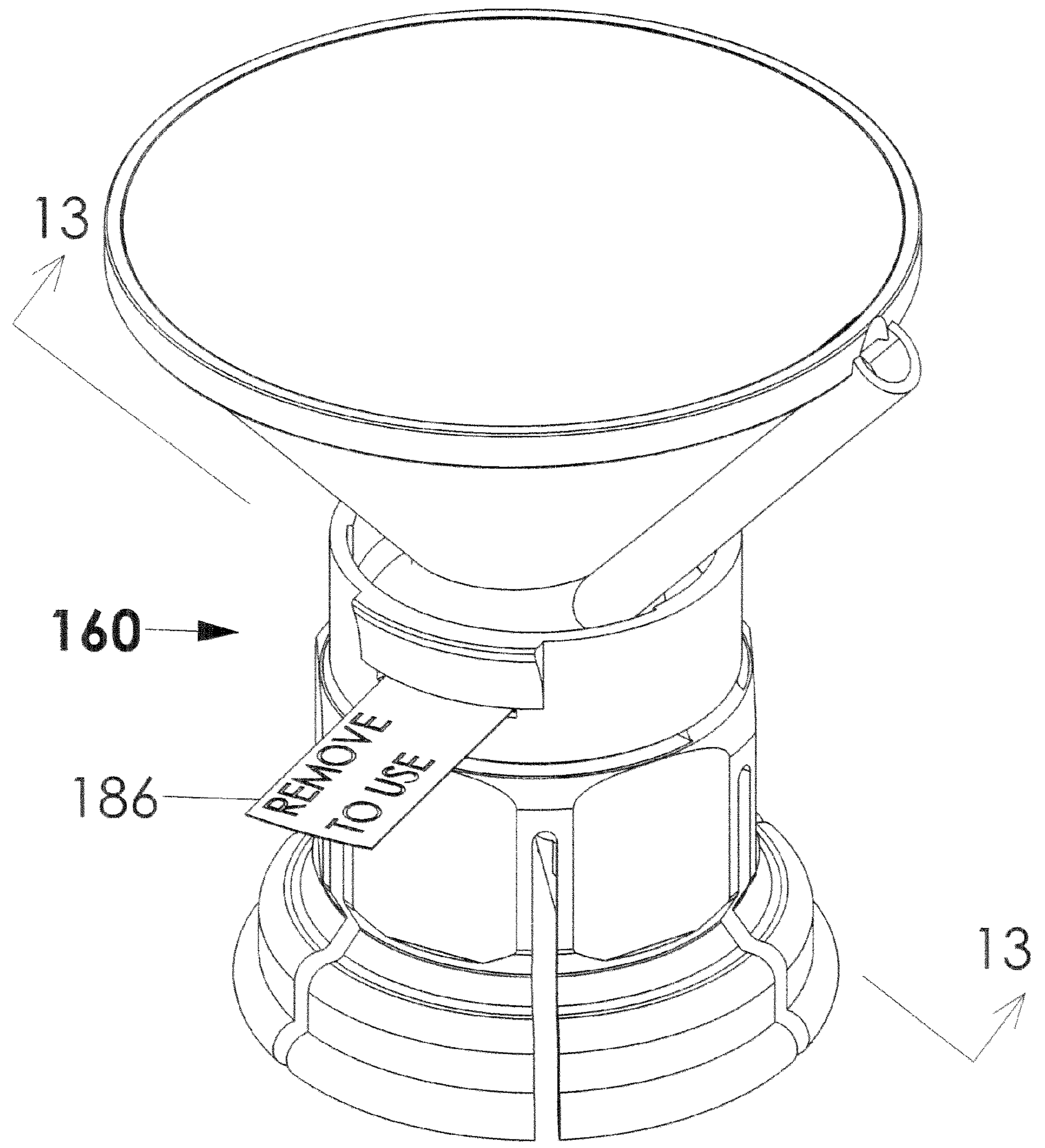
FIG. 8 is a perspective view of another embodiment of a cap adapter for a medicament vial in accordance with the present disclosure.
Figure 10:
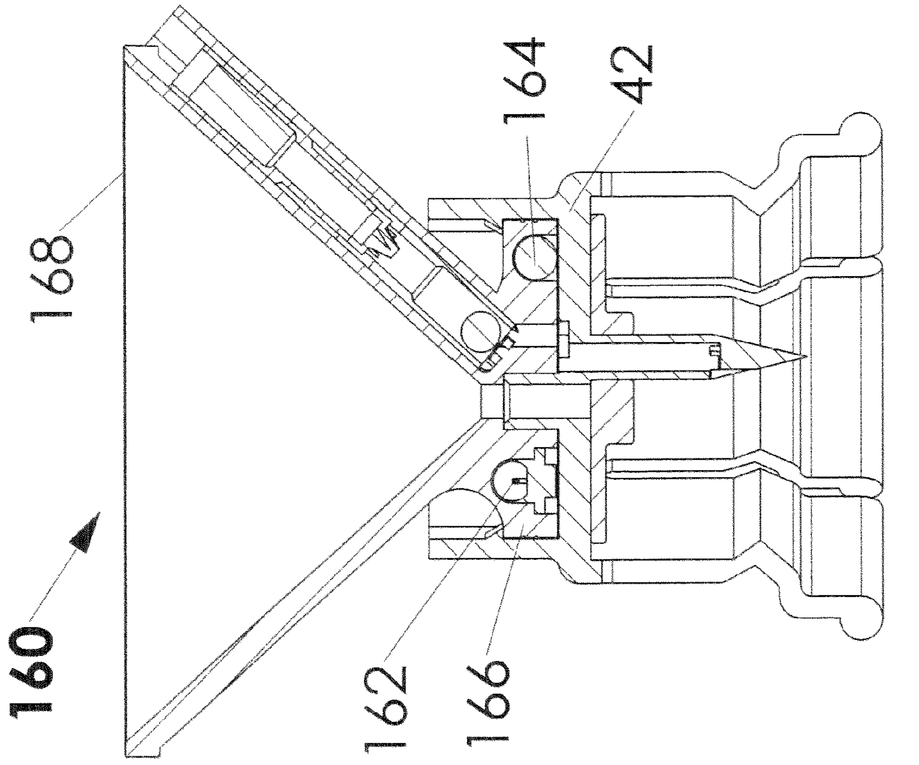
FIG. 10 is a cross-sectional view of the cap adapter of FIG. 9, taken through the line 10-10 in FIG. 9.
Figure 9:
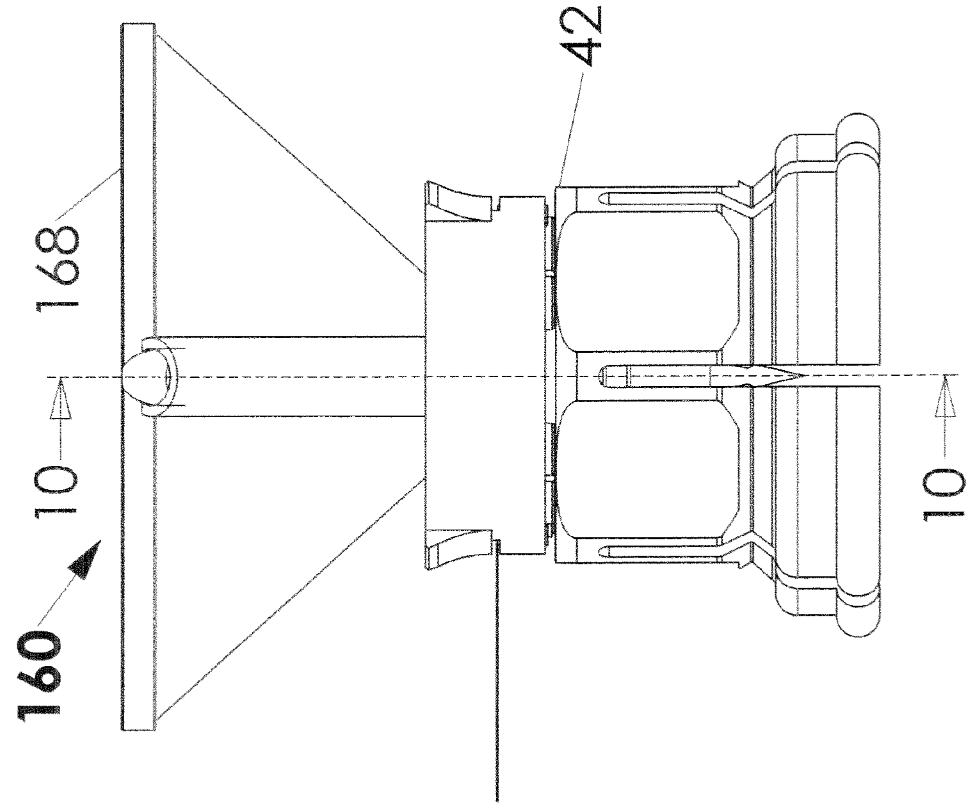
FIG. 9 is a right side elevation view of the cap adapter of FIG. 8.

With reference to FIGS. 8, 17 and 18, in certain embodiments the cap adapter 160 may be initially shipped with a removable pull tab 186. The pull tab 186 is made of a ribbon or tape of insulative material, and it provides an insulator between the conductive layer 184 on one of the tabs 180 and the adjacent first and second electrical leads 174, 176, as shown in FIG. 18. The tab 186 thus prevents inadvertent contact between the leads 174, 176 and the conductive layer 184. Inadvertent squeezing forces applied to the tabs 180 thus do not cause the LED 162 to illuminate, which preserves the lifespan of the batten 164. To use the cap adapter 160 for the first time, the user removes the pull tab 186 by grasping the protruding portion and pulling. In certain embodiments, removable pull tabs 186 may be provided for both tabs 180 of the cap adapter 160.

Figure 21:
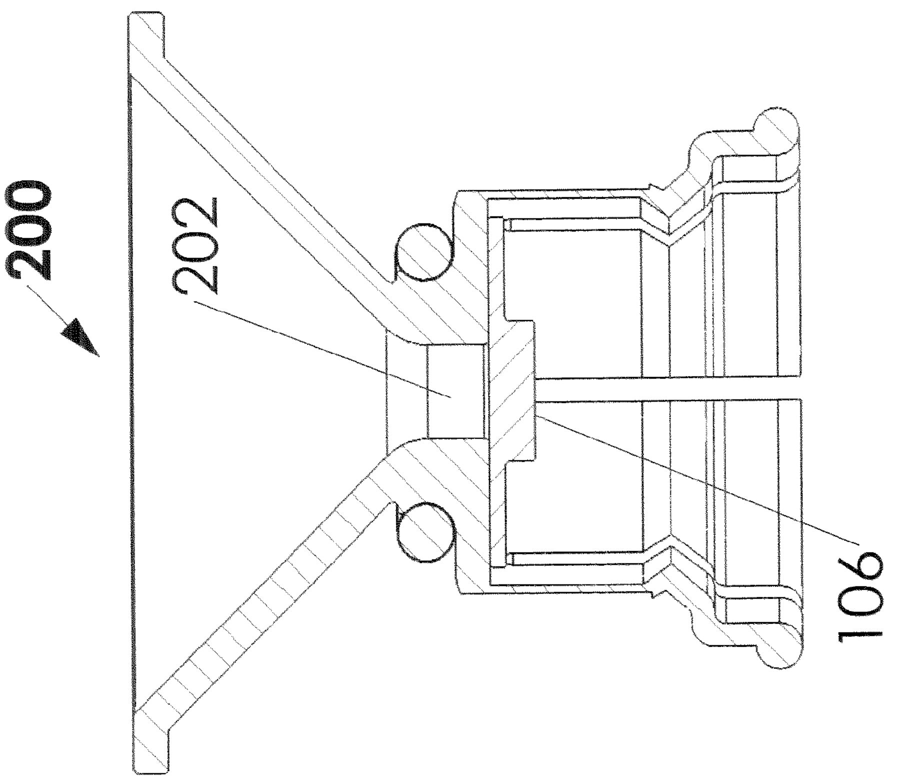
FIG. 21 is a cross-sectional view of the cap adapter of FIG. 20, taken through the line 21-21 in FIG. 20.
Figure 20:
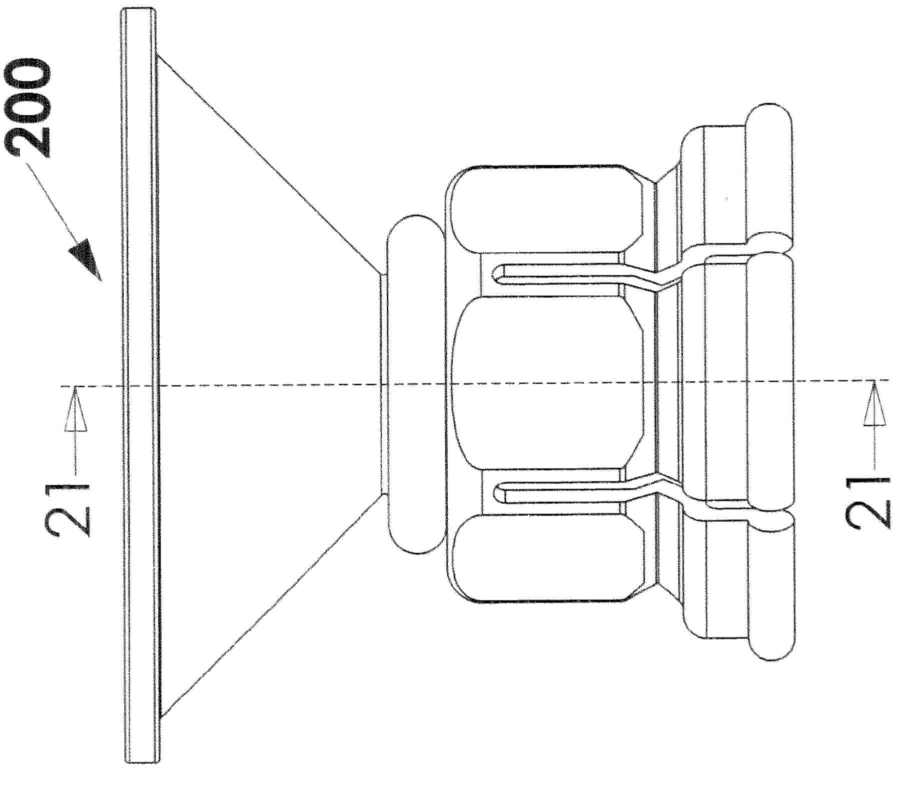
FIG. 20 is a front elevation view of another embodiment of a cap adapter for a medicament vial in accordance with the present disclosure.

FIGS. 20 and 21 illustrate another embodiment of the present cap adapter 200 for a medicament vial. The cap adapter 200 is similar to the cap adapter 40 described above and illustrated in FIGS. 1-7. The cap adapter 200, however, does not include a spike comprising a second lumen. The cap adapter 200 further does not include a vent passage, filter, secondary sealing member, or axial connecting passage. The cap adapter 200 of FIGS. 20 and 21 is thus advantageously less expensive to manufacture than the cap adapters 40, 160 described above, because it is less complex. Further, the cap adapter 200 of FIGS. 20 and 21 advantageously includes a needle entrance lumen 202 that is larger than the first lumen 44 of the cap adapter 40 of FIGS. 1-7.

To withdraw medicament from a vial using the cap adapter 200 of FIGS. 20 and 21, the user secures the cap adapter 200 over the medicament vial substantially as described above with respect to the embodiment of FIGS. 1-7. By contrast, however, there is no step of a spike penetrating a sealing stopper on the vial when using the cap adapter 200 of FIGS. 20 and 21. The user then inserts a syringe needle through the secondary seal 106 (FIG. 21) and the vial sealing stopper and into the interior of the vial. The larger lumen 202 advantageously provides a larger target for the user as he or she guides the syringe needle. The user may withdraw liquid from the vial by drawing back on the syringe plunger after the needle has been inserted into the vial. To facilitate easy drawback of the plunger, the user may pressurize the vial by drawing the plunger back prior to penetrating the secondary seal and the vial sealing stopper, and then injecting air into the vial.

Figure 22:
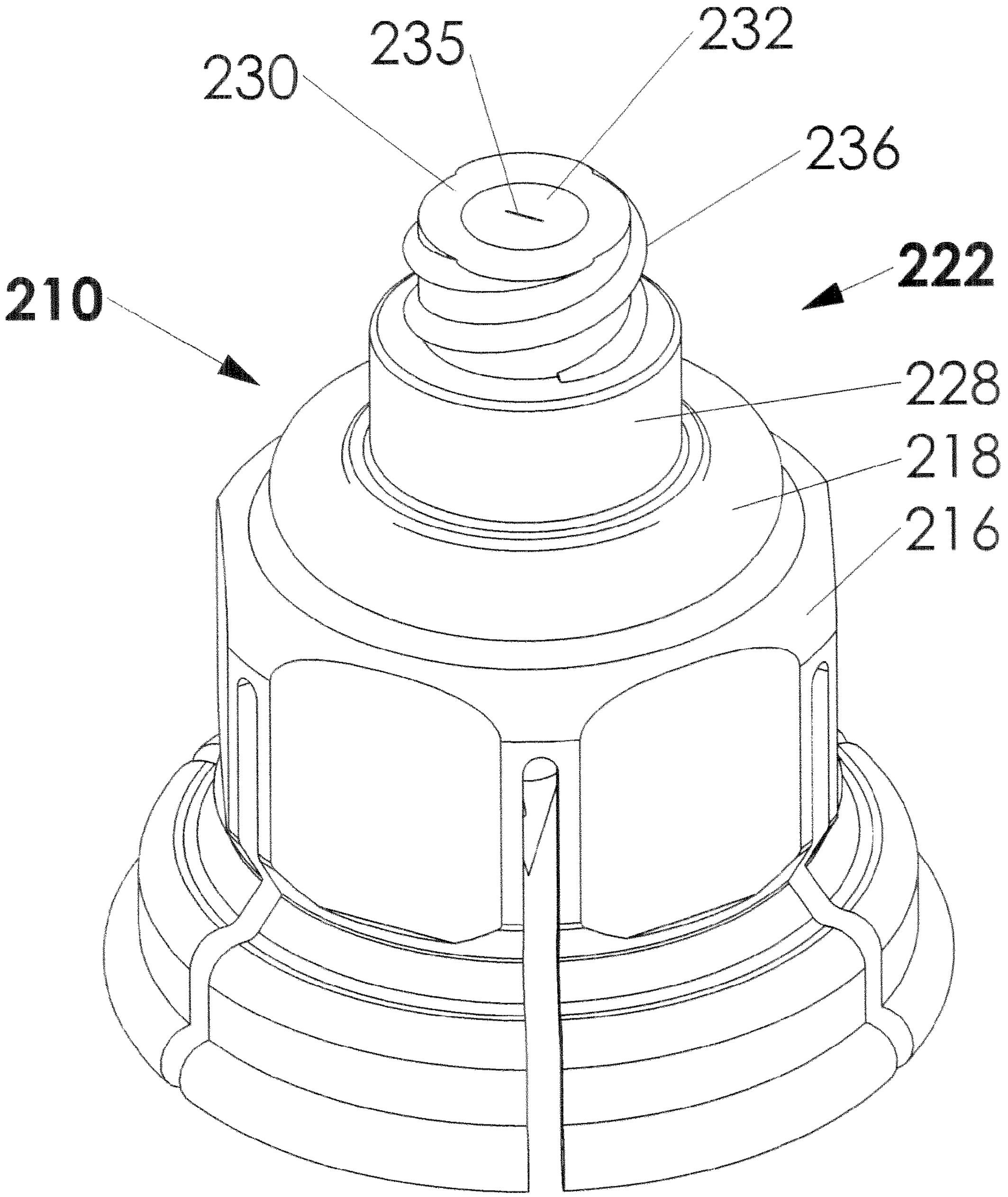
FIG. 22 is a perspective view of another embodiment of a cap adapter for a medicament vial in accordance with the present disclosure.
Figure 24:
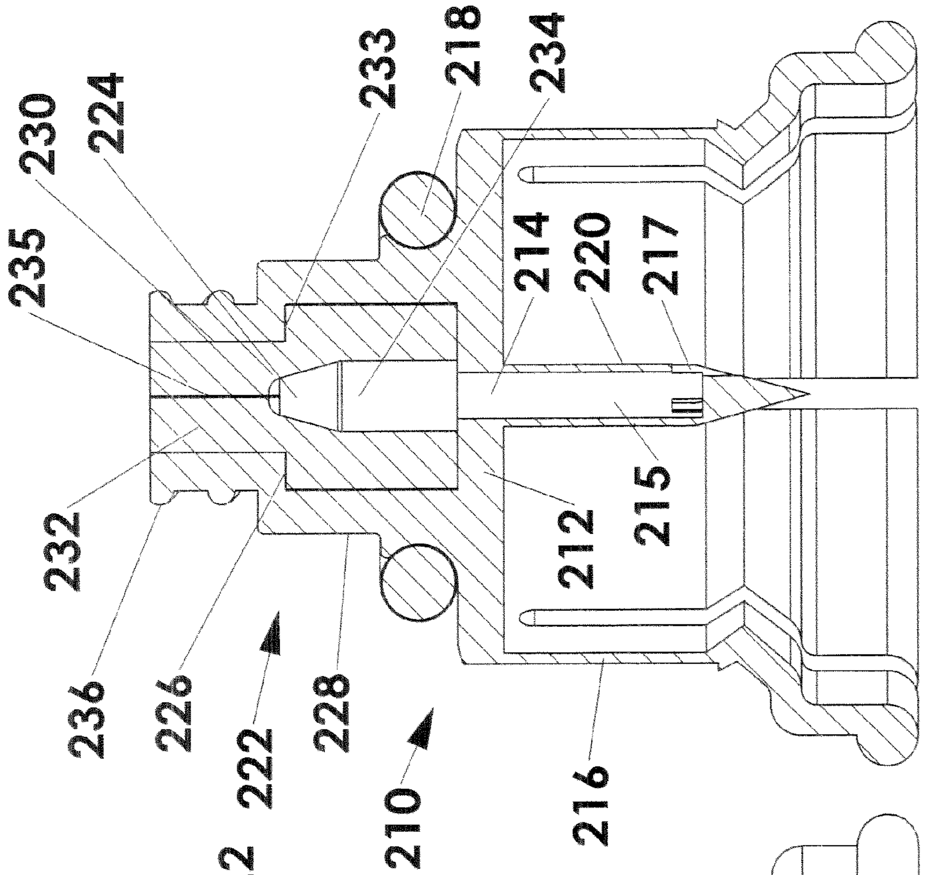
FIG. 24 is a cross-sectional view of the cap adapter of FIG. 23, taken through the line 24-24 in FIG. 23.
Figure 23:
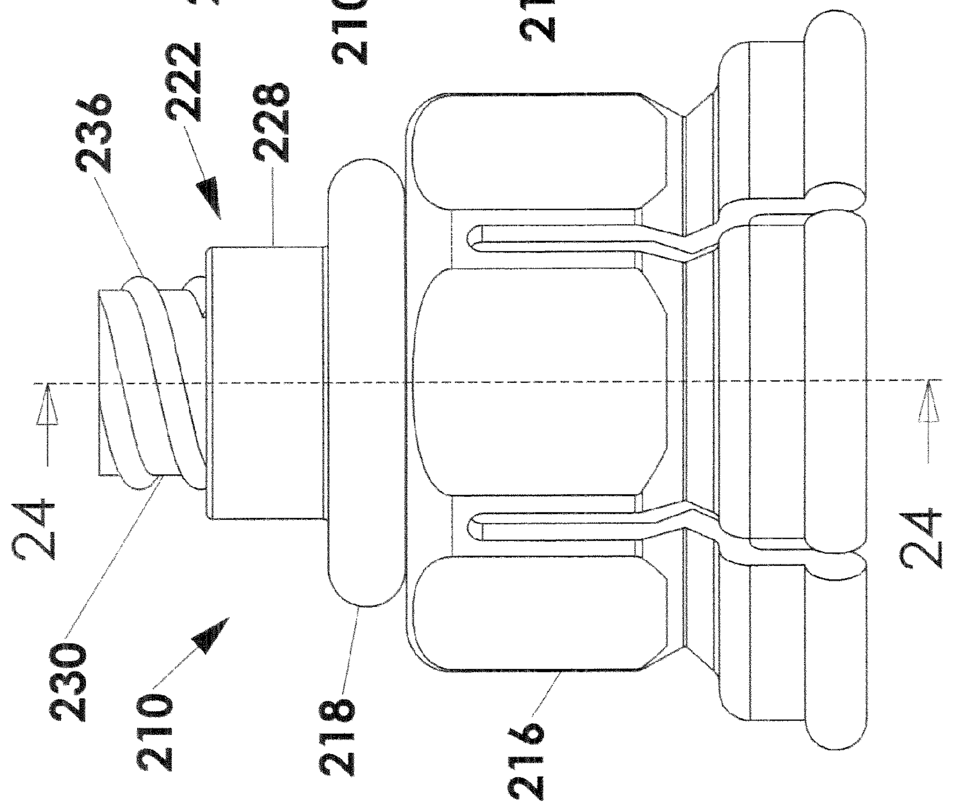
FIG. 23 is a front elevation view of the cap adapter of FIG. 23.

FIGS. 22-24 illustrate another embodiment of the present cap adapter 210 for a medicament vial. The cap adapter 210 is needleless, meaning that it is adapted to operate with a syringe having no hypodermic needle. With reference to FIG. 24, the cap adapter 210 includes a transverse wall portion 212 having a central, orifice 214 and a vial-engaging portion 216 extending distally from the wall portion 212. The cap adapter 210 further includes a light source 218, which in the illustrated embodiment is a chemiluminescent ring 218 similar to that described above.

A hollow spike 220 extends distally from the transverse wall portion 212, terminating in a sharp distal tip 215. The interior of the spike 220 defines a lumen 217 that is aligned with and in fluid communication with the central orifice 214. The lumen 215 terminates in an inlet port 219 proximal to the distal tip 215. When the cap adapter 210 is secured to a medicament vial, the distal tip 215 of the spike 220 pierces the vial sealing stopper 138 and opens fluid communication between the interior of the vial and the central orifice 214.

A female luer fitting 222 extends proximally from the wall portion 212. The interior of the female luer fitting 222 includes an internal annular shoulder 226 between a distal portion 228 having a first inside diameter and a proximal portion 230 having a second inside diameter that is less than the first inside diameter. The interior of the female luer fitting 222 receives a resilient elastomeric sealing member 232 that conforms to the interior of the female luer fitting 222. The sealing member 232 includes an external annular shoulder 233 that seats against the internal annular shoulder 226 of the female liter fitting 222 to fix the axial position of the sealing member 232 relative to the female luer fitting 222. The sealing member 232 has a distal surface that seats against the proximal surface of the transverse wall 212, and it has an interior cavity 234 with an open distal end that communicates with the central orifice 214 of the transverse wall 212. The proximal portion of the sealing member 232 includes a slit 235 that opens fluid communication into the interior cavity 234 and through the sealing member 232 when forced open, as described below.

The proximal end of the female liter fitting 222 is configured to receive a male luer fitting (not shown) that is fixed to the distal end of a needleless syringe (not shown). As is well-known in the art, the male luer fitting is threaded for engagement with a thread 236 on the female luer fining 222. When the male luer fitting is threaded into the female luer fitting 222, it forces open the slit 235 in the sealing member 232. With the syringe engaging the female luer fitting 222 and the sealing member 232 forced open, fluid communication is established between the cavity 234 and the syringe. The syringe can thus withdraw liquid from a vial to which the cap adapter 210 is attached.

FIGS. 25-30 illustrate another embodiment of the present cap adapter 250 for a medicament vial 128. The cap adapter 250 includes a vial-engaging element 260 that is similar in many respects to the cap adapter 40 described above and illustrated in FIGS. 1-7. For instance, the vial-engaging element 260 includes a transverse wall 252 having a first lumen 254 extending axially through its center. A spike 256, defining a second lumen 258 (FIGS. 26 and 29), extends distally from the transverse wall 252, at a position radially offset from the first lumen 254. A circumferential axial wall 264 extends proximally from the transverse wall 252, and a plurality of clamping members 262 extend distally from the periphery of the transverse wall 252. The vial-engaging element 260 may advantageously include a shield element and a one-way valve, as described above with respect to the cap adapter 40 of FIGS. 1-7. However, for clarity the shield element and the one-way valve have been omitted from FIGS. 25-30.

In contrast to the embodiments described above, which may include as many as six or more closely spaced clamping members 48, the vial-engaging element 260 of the cap adaptor 250 of FIGS. 25-30 advantageously includes no more than three or four widely spaced clamping members 262. It will be appreciated that the present cap adapters 40, 160, 200, 210, 250 may include any number of clamping members, and the illustrated configurations are not limiting.

Figure 25:
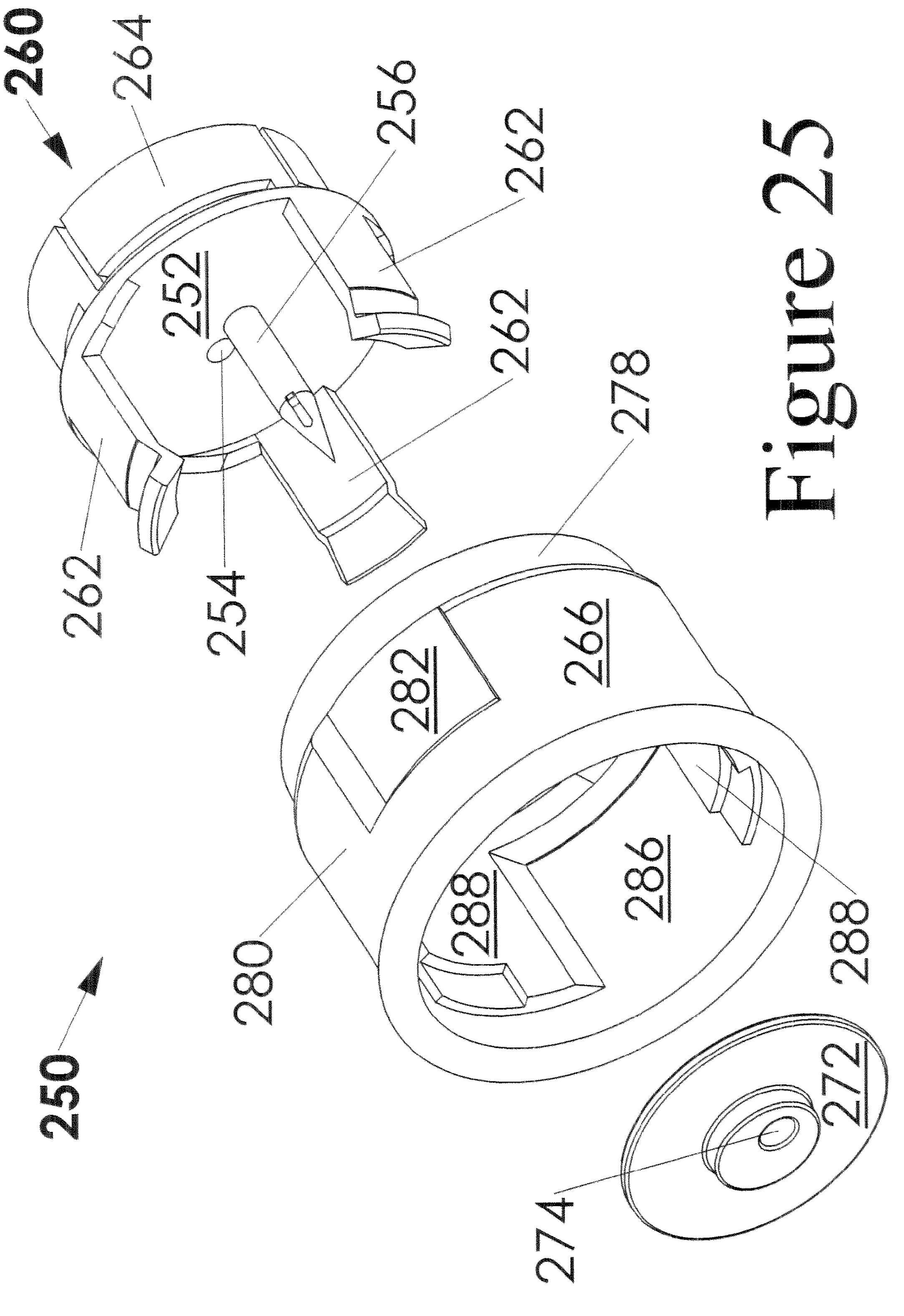
FIG. 25 is an exploded bottom perspective view of another embodiment of a cap adapter, which includes a locking sleeve, in accordance with the present disclosure.
Figure 26:
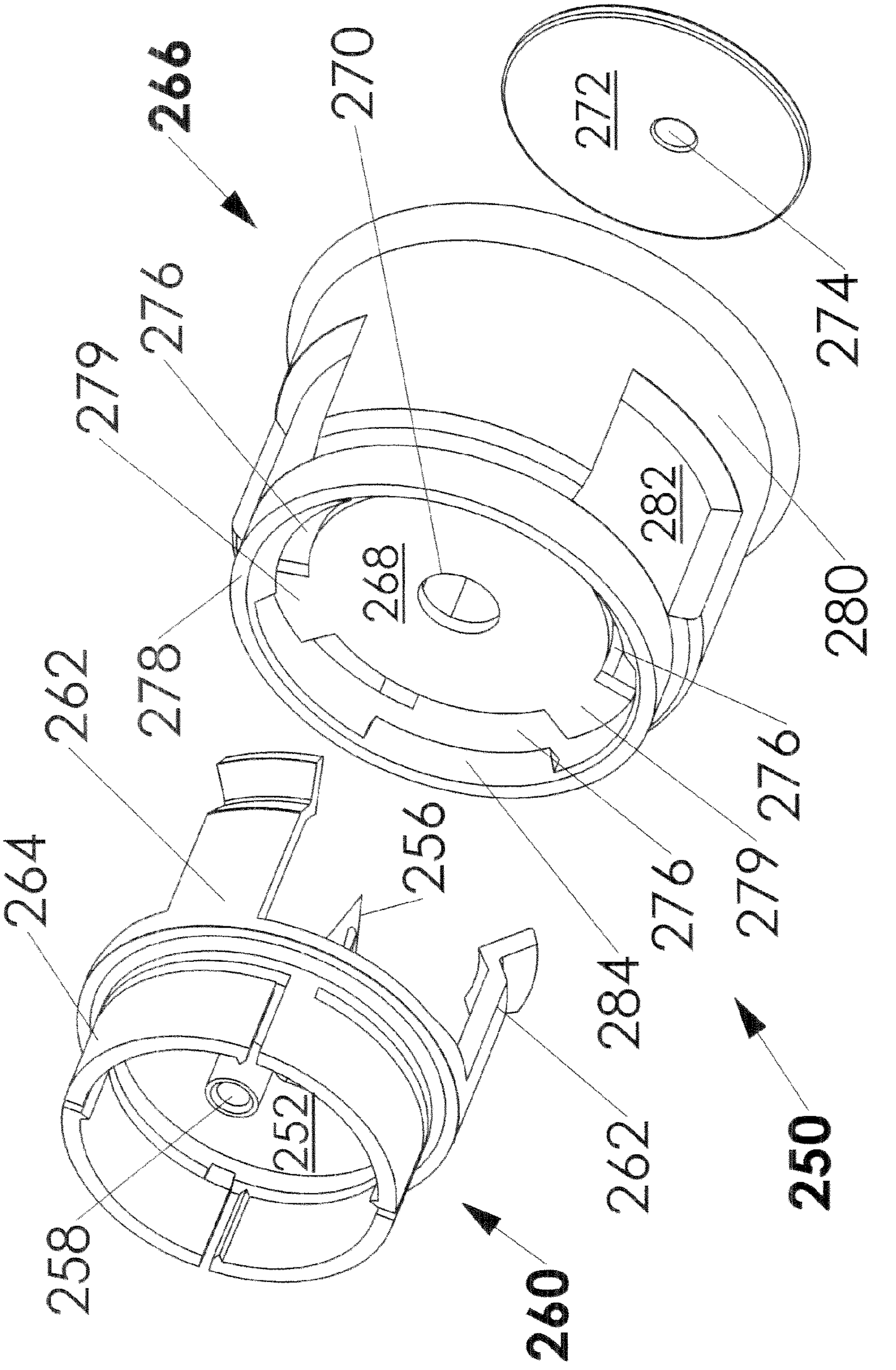
FIG. 26 is an exploded top perspective view of the cap adapter of FIG. 25.
Figure 27:
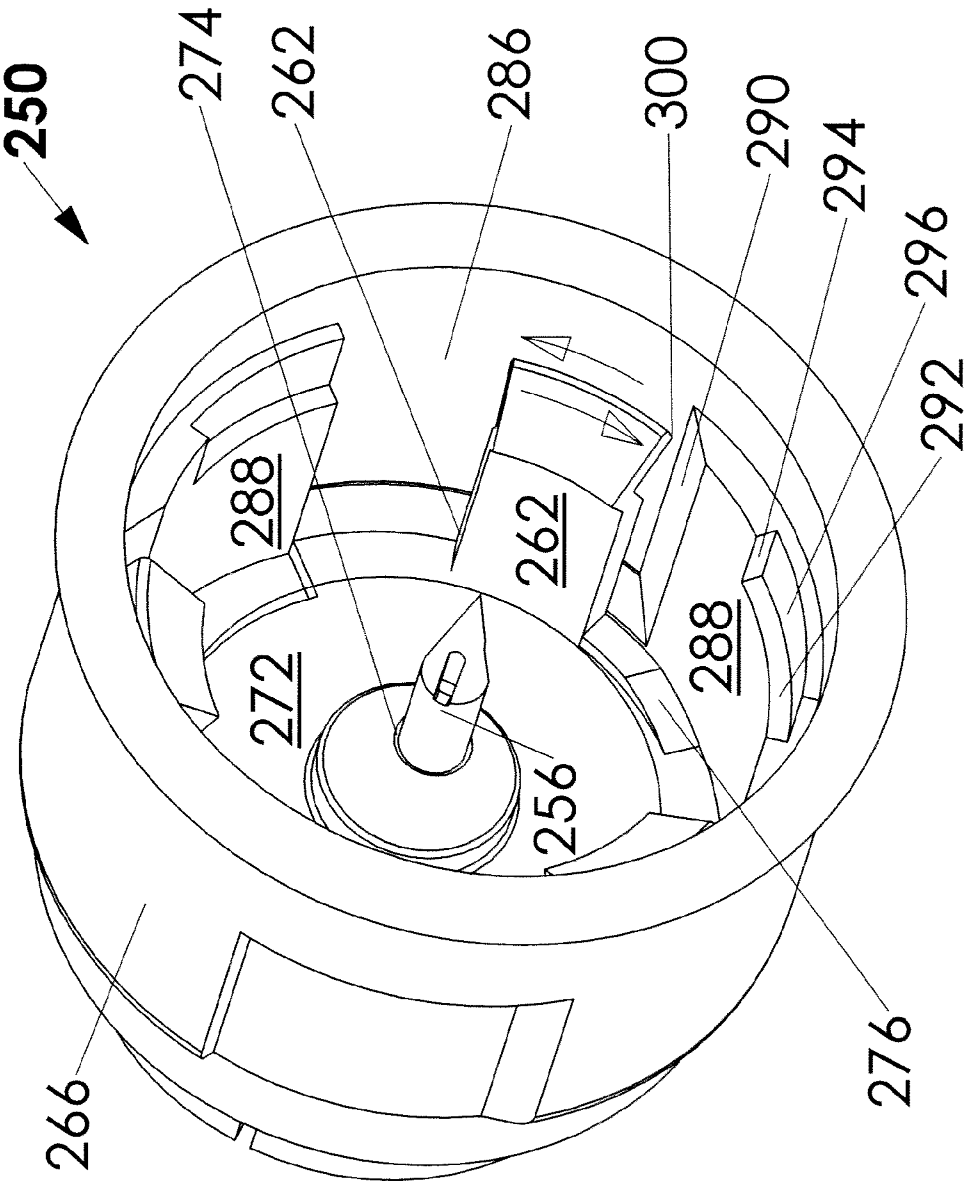
FIG. 27 is an assembled bottom perspective view of the cap adapter of FIG. 25, showing the cap adapter and the locking sleeve in a first relative rotated position.

As best shown in FIGS. 25-27, the cap adapter 250 further includes a locking sleeve 266. The locking sleeve 266 is substantially cylindrical, and includes a proximal transverse wall 268 having a central aperture 270 (FIG. 26). A secondary seal 272, which seats against a distal surface of the transverse wall 252, includes an off-center opening 274 that receives the spike 256. The transverse wall 268 of the locking sleeve 266 is fixed to the interior of a circumferential rim 278 by a plurality of radial spokes 279 separated by circumferentially spaced slots 276. The locking sleeve 266 has an outer surface 280 that may advantageously include a plurality of circumferentially-spaced depressions 282 that provide gripping surfaces for the user when relatively rotating the vial-engaging element 260 and the locking sleeve 266, as described in further detail below.

Figure 29:
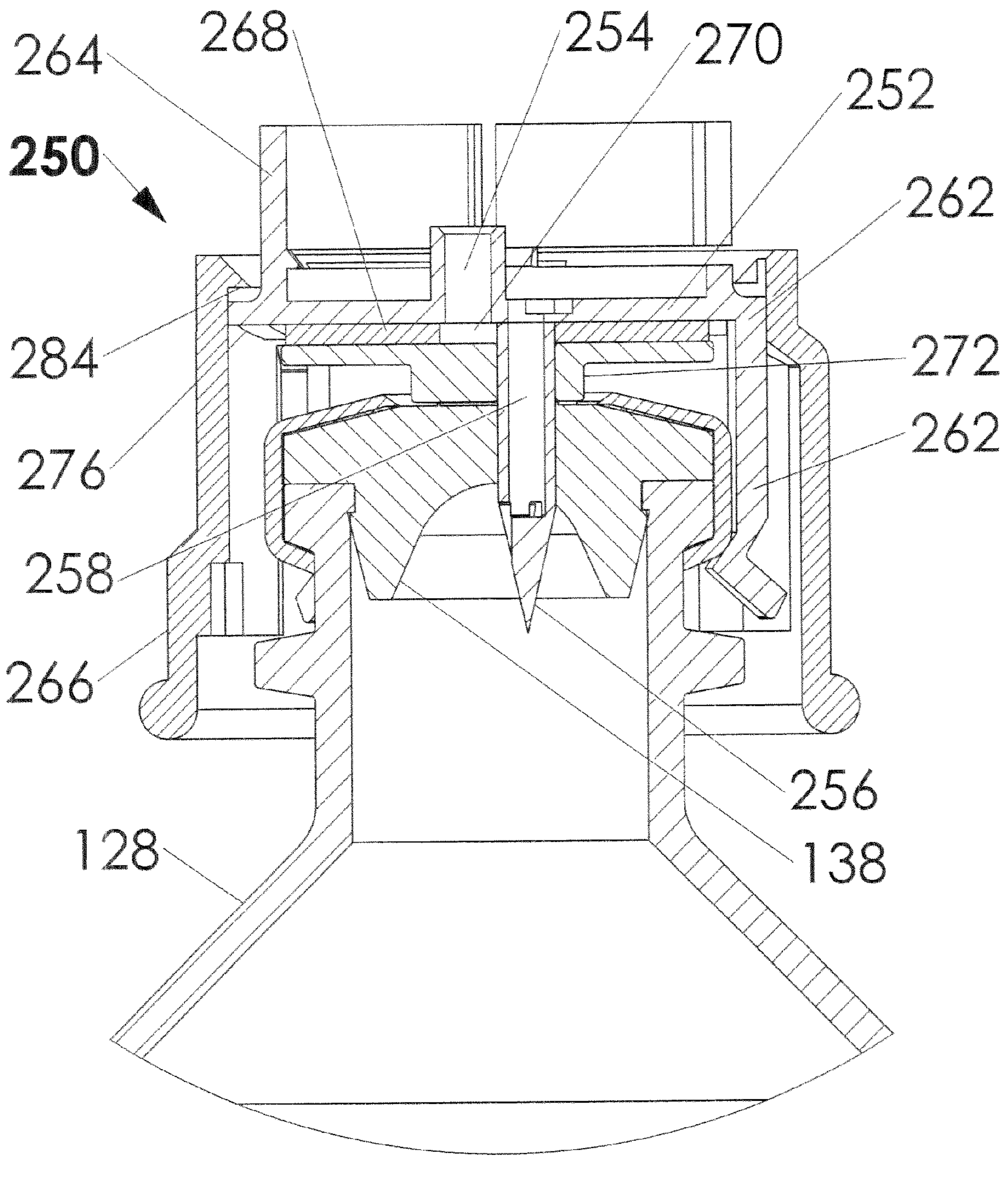
FIG. 29 is a cross-sectional view of the assembled cap adapter of FIG. 27 engaging a medicament vial.

With reference to FIGS. 27 and 29, in the assembled cap adapter 250 the transverse walls 252, 268 of the vial-engaging element 260 and the locking sleeve 266, respectively, abut one another. In this configuration, the clamping members 262 of the vial-engaging element 260 extend through the slots 276 in the transverse wall 268 of the locking sleeve 266, and the spike 256 extends through the aperture 270 of the locking sleeve 266 and the aperture 274 of the secondary seal 272. A proximal inner edge of the locking sleeve 266 includes a lip or detent 284 that extends radially inwardly so as to engage the periphery of the proximal surface of the transverse wall 252 of the vial-engaging member 250, thereby to prevent the separation of the cap adapter components in the axial direction.

FIG. 27 illustrates the cap adapter 250 and locking sleeve 266 in an assembled, unlocked configuration. An inner surface 286 of the locking sleeve 266 includes three circumferentially spaced elevated surfaces 288. The elevated surfaces 288 are configured and located so as to engage the clamping members 262, as described in detail below.

Figure 28:
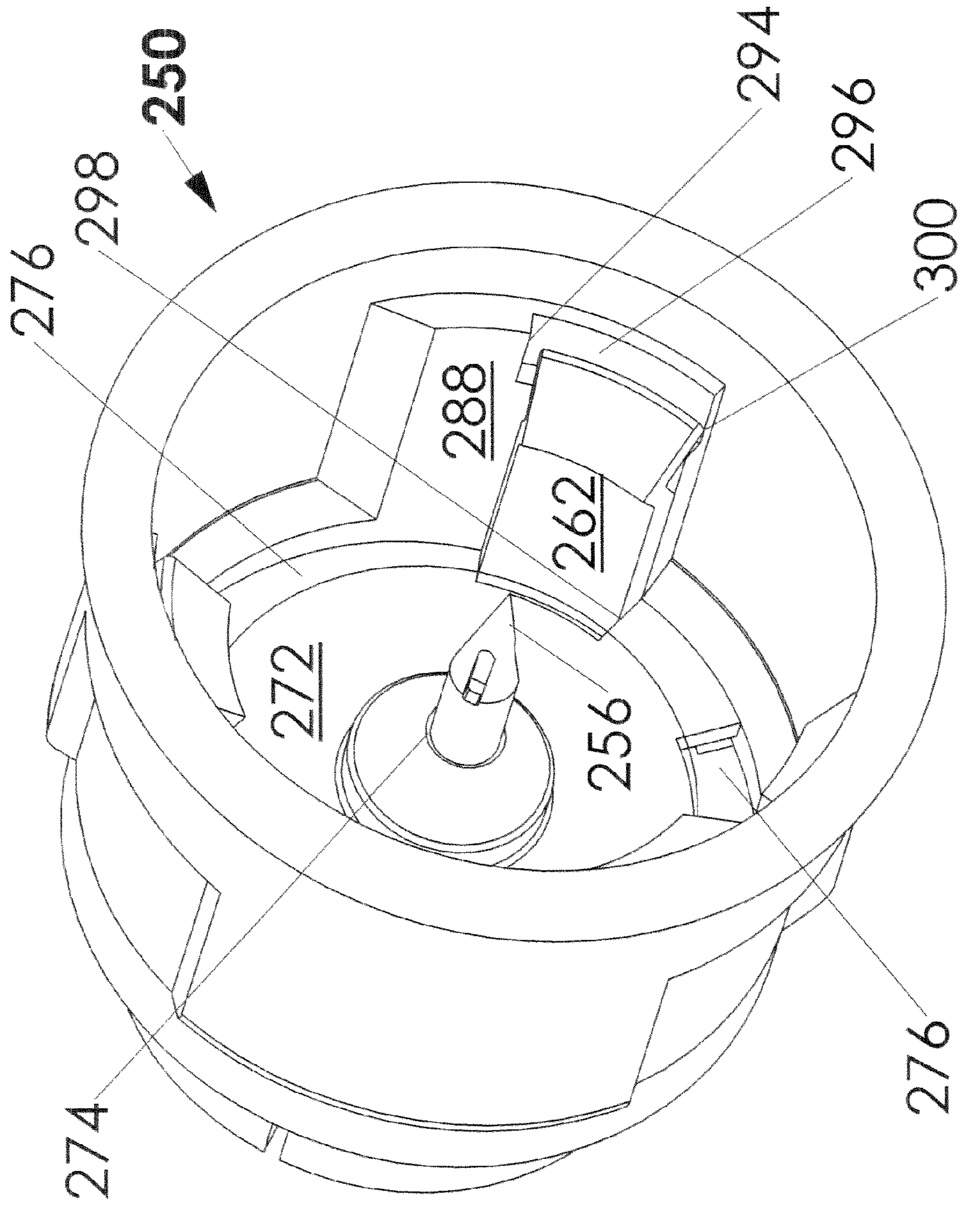
FIG. 28 is an assembled bottom perspective view of the cap adapter of FIG. 25, showing the cap adapter and the locking sleeve in a second relative rotated position.

With continued reference to FIG. 27, each of the elevated surfaces 288 includes a ramped surface 290 that extends axially, and a clamping surface 292 that extends circumferentially and faces distally. When the vial-engaging element 260 and the locking sleeve 266 are rotated, relative to one another, as indicated by the oppositely directed arrows in FIG. 27, causing the clamping members 262 to ride up over the ramped surfaces 290 and onto the elevated surfaces 288, which flexes the clamping members 262 radially inward. After riding over the elevated surfaces 288, the clamping members 262 pass over radial locking surfaces 294, which extend substantially perpendicularly to the inner surface 286 of the locking sleeve 266. Passing over the locking surfaces 294, the clamping members 262 snap radially outward into retaining cavities 296, as shown in FIG. 28. Once the clamping members 262 are located in the retaining cavities 296, end walls 298 of the slots 276 prevent further relative rotation of the vial-engaging element 260 and the locking sleeve 266, and the radial locking surfaces 294 prevent reverse relative rotation.

Figure 30:
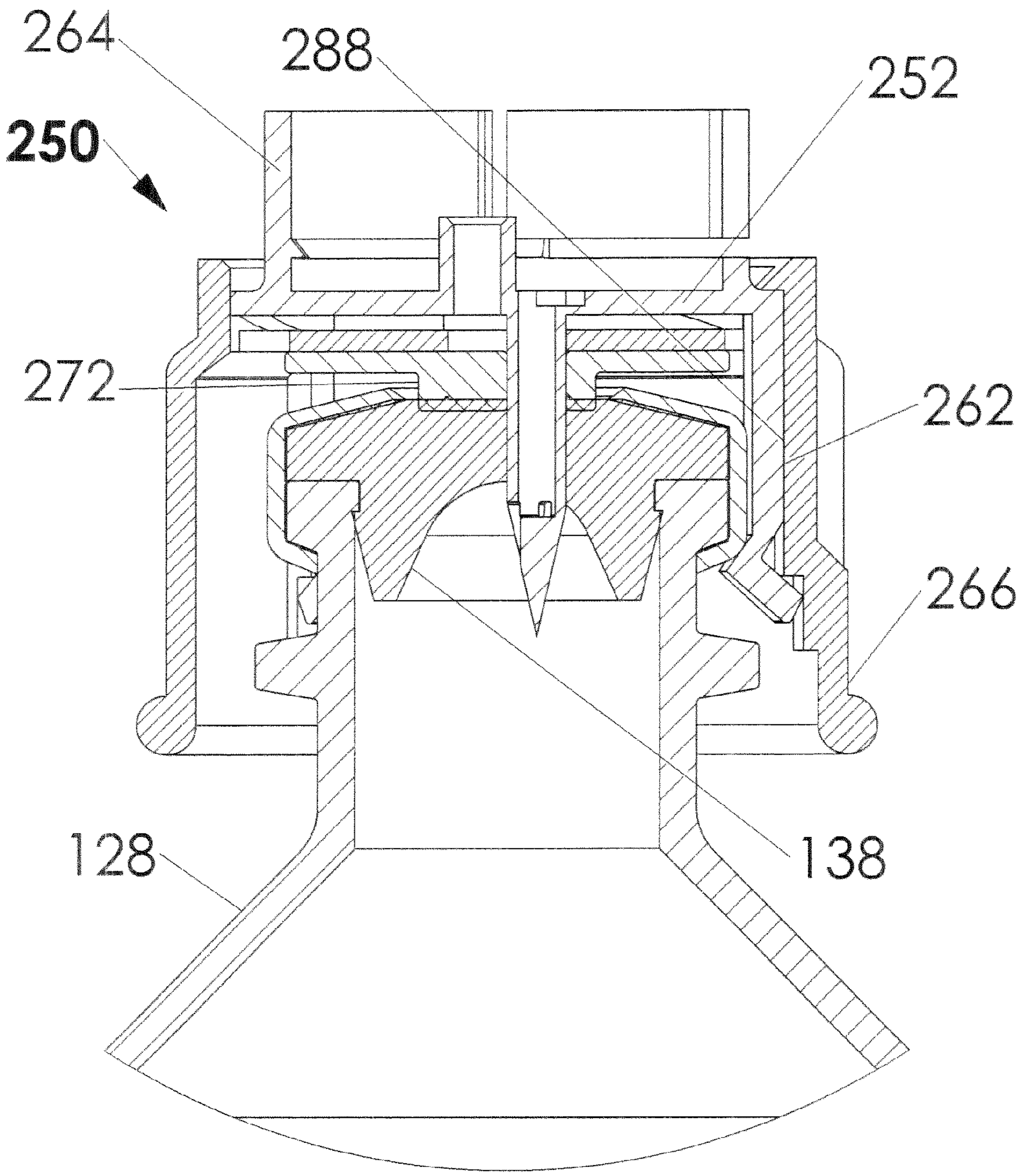
FIG. 30 is a cross-sectional view of the assembled cap adapter of FIG. 28 engaging a medicament vial.

As the clamping members 262 pass over the radial locking surfaces 294, a leading edge 300 of each clamping member 262 engages a corresponding clamping surface 292. The clamping surfaces 292 are ramped, so that as the vial-engaging element 260 continues rotating relative to the locking sleeve 266, the vial-engaging element 260 is forced distally relative to the locking sleeve 266. This relative axial movement is illustrated in FIGS. 29 and 30.

FIG. 29 illustrates the cap adapter 250 engaging a medicament vial 128. The cap adapter 250 is in the unlocked position of relative rotation, which is illustrated in FIG. 27. In this configuration, the spike 256 extends through the sealing stopper 138, and the clamping members 262 secure the cap adapter 250 to the medicament vial 128 as described above with respect to the previous embodiments. The secondary seal 272 may abut the sealing stopper 138, or it may be closely spaced therefrom as shown in FIG. 29. To further secure the cap adapter 250 to the medicament vial 128, the user rotates the locking sleeve 266 with respect to the vial-engaging element 260 in the manner described with respect to FIGS. 27 and 28. With reference to FIG. 30, which illustrates the locked position of relative rotation, the clamping members 262 abut the elevated surfaces 288, preventing the clamping members 262 from flexing radially outwardly. The cap adapter 250 is thus locked onto the medicament vial 128. Further, the relative axial movement of the vial-engaging element 260 and the locking sleeve 266, described above, forces the secondary seal 272 distally into firm abutting engagement with the sealing stopper 138. The secondary seal 272 thus creates a substantially fluid-tight seal against the proximal surface of the sealing stopper 138. Once the cap adapter 250 is in the illustrated locked configuration, the user can withdraw medicament from the vial 128 in the same manner as described above with respect to the cap adapter 40 of FIGS. 1-7. Because the locking surfaces 294 (FIG. 28) prevent reverse relative rotation of the vial-engaging element 260 and the locking sleeve 266, and because the elevated surfaces 288 prevent outward radial flexing of the clamping members 262, the cap adapter 250 is permanently secured to the vial 128 and cannot be removed without damaging the cap adapter 250 and/or the vial 128. The cap adapter 250 can thus substantially reduce the likelihood that the contents of the vial 128 will escape into the ambient environment.

Figure 31:
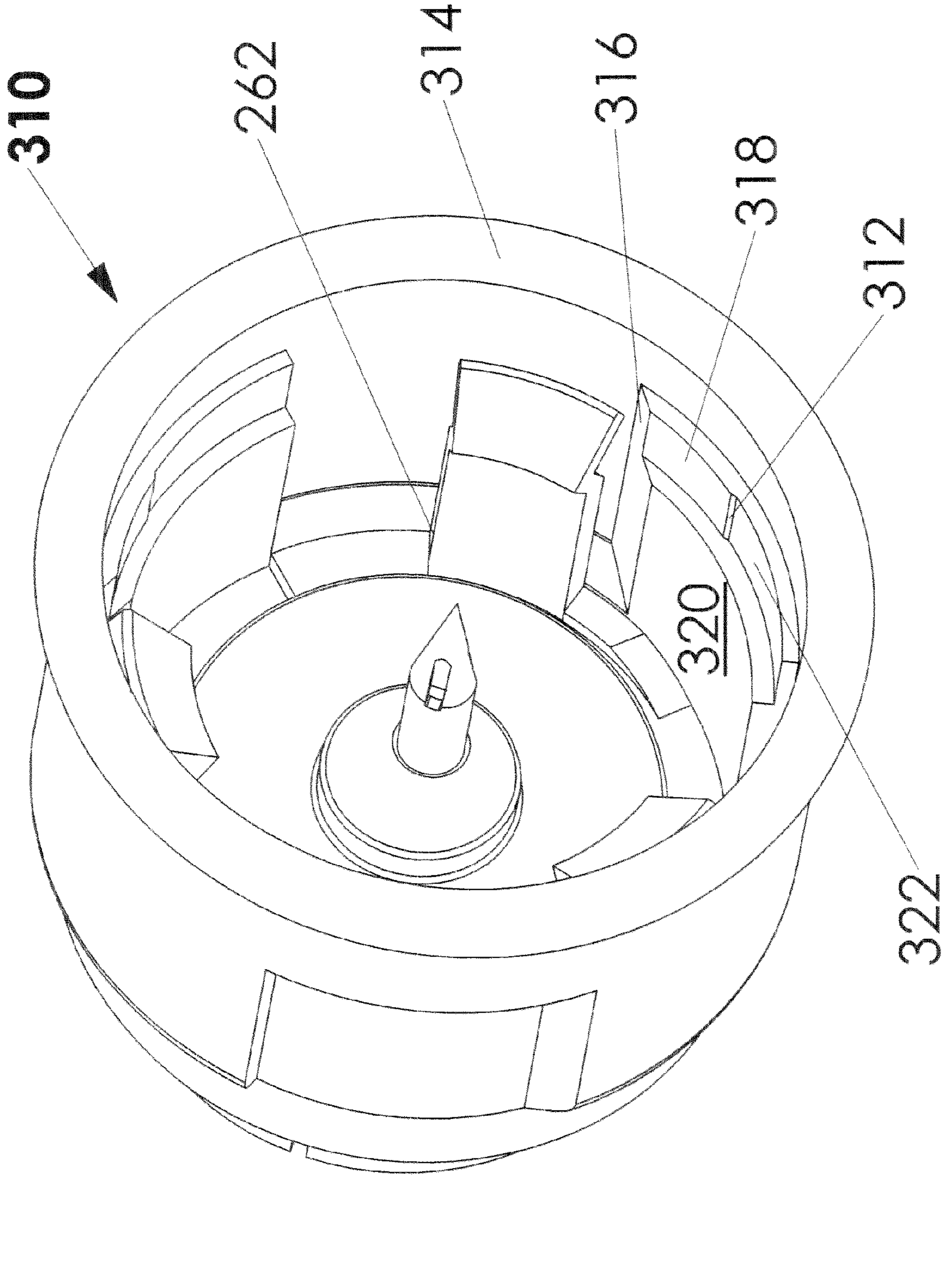
FIG. 31 is an assembled bottom perspective view of another embodiment of a cap adapter with a locking sleeve for a medicament vial in accordance with the present disclosure, showing the cap adapter and the locking sleeve in a first relative rotated position.
Figure 32:
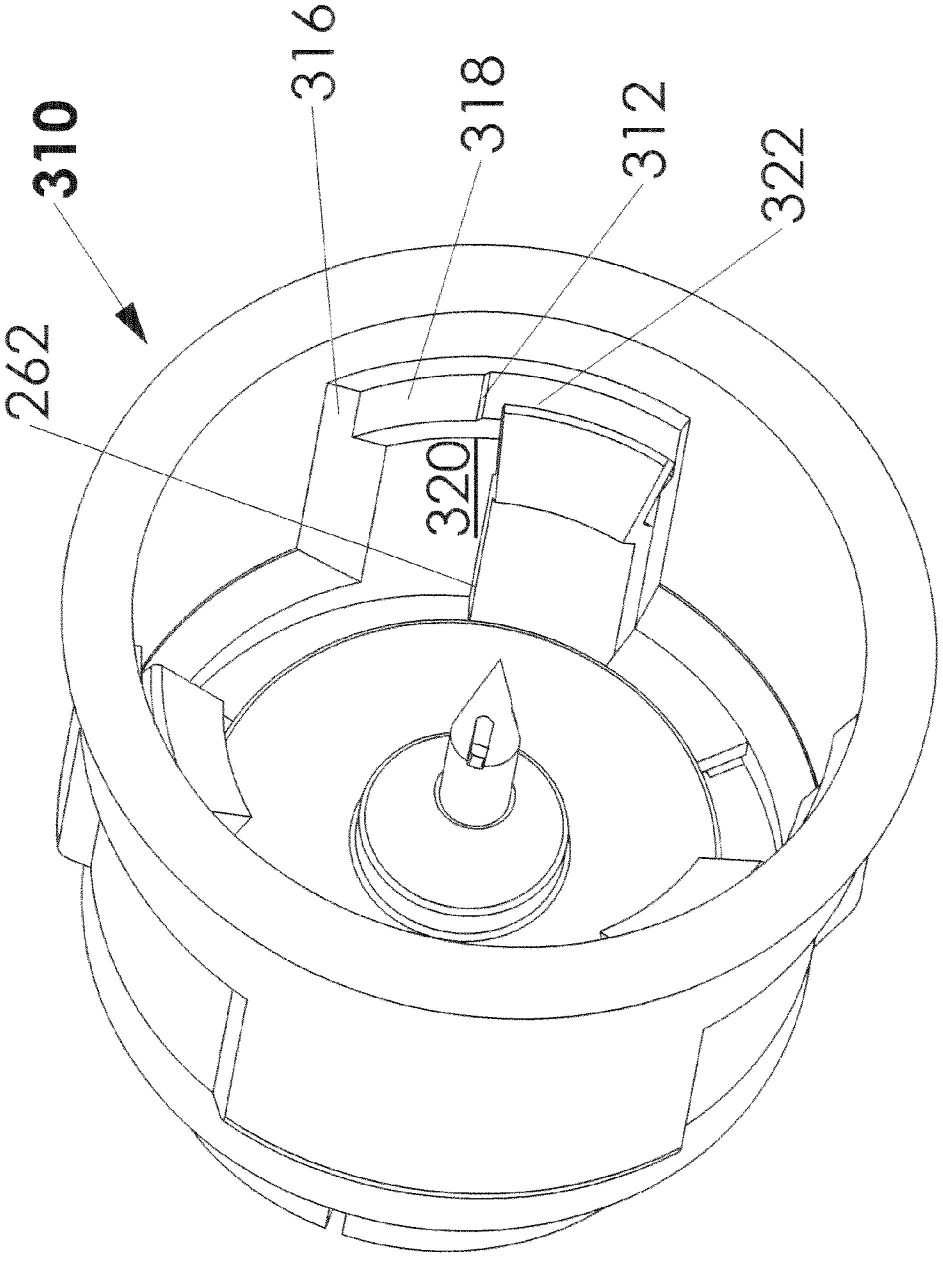
FIG. 32 is an assembled bottom perspective view of the cap adapter of FIG. 31, showing the cap adapter and the locking sleeve in a second relative rotated position.

FIGS. 31 and 32 illustrate another embodiment of the present cap adapter 310 for a medicament vial. The cap adapter 310 is identical to the cap adapter 250 illustrated in FIGS. 25-30, except for the structure on the interior surface of the locking sleeve. Specifically, the cap adaptor 310 includes a locking sleeve 314 that includes, on its interior surface, a plurality of circumferentially-spaced locking structures, each of which comprises an elevated surface 320 adjacent the proximal end of the sleeve 314, and a detent structure, adjacent a distal edge of the elevated surface. The detent structure is radially recessed relative to the elevated surface 320; that is, it has a lower elevation relative to the interior surface of the locking sleeve 314 than does the elevated surface 320. Each detent structure comprises a first, upper step 318 and a second, lower step 322, separated by an axial detent lip 312. Each of the locking structures also includes an axially-extending ramped edge 316 that is contiguous with the elevated surface 320 and the first step 318.

When the vial-engaging element 260 and the locking sleeve 314 are rotated relative to one another, as indicated by the oppositely directed arrows in FIG. 31, each of the clamping members 262 rides up over a corresponding ramped edge 316 and onto an adjacent first step 318. The first steps 318 flex the clamping members 262 radially inward. After riding over its associated first step, 318, each of the clamping members 262 passes over a detent lip 312 and onto the adjacent (and lower) second step 322. Passing over the lips 312, the clamping members 262 snap radially outward onto the second steps 322, as shown in FIG. 32. Once the clamping members 262 are seated on the second steps 322, the lips 312 resist, but do not prevent, reverse relative rotation. The embodiment 310 of FIGS. 31 and 32 can thus be removed from the medicament vial 128 by reverse relative rotation of the vial-engaging element 260 and the locking sleeve 314. The lips 312 provide a tactile cue that the cap adapter 310 is fully secured on the medicament vial 128, and also provide light resistance against accidental reverse relative rotation.

The above description presents the best mode contemplated for carrying out the present cap adapters and associated methods, and of the manner and process of making and using them, in such full, clear, concise, and exact terms as to enable any person skilled in the art to which it pertains to make and use these cap adapters. These cap adapters and associated methods are, however, susceptible to modifications and alternate constructions from that discussed above that are fully equivalent. Consequently, these cap adapters and associated methods are not limited to the particular embodiments disclosed. On the contrary, these cap adapters and associated methods cover all modifications and alternate constructions coming within the spirit and scope of the cap adapters and associated methods as generally expressed by the following claims, which particularly point out and distinctly claim the subject matter of the cap adapters and associated methods.

What is claimed is:

1. A cap adapter configured for the transfer of liquid from a medicament vial into a syringe, the vial having a mouth closed by a sealing stopper, the cap adapter comprising:

- a transverse wall portion configured to fit over the mouth of the vial and having a proximal side and a distal side;
- a lumen passing through the transverse wall portion and defining a port on the proximal side of the transverse wall portion;
- a vial-engaging portion extending distally from the transverse wall portion and configured for removably attaching the cap adapter to the vial with the distal side of the transverse wall portion facing the sealing stopper;
- a shield extending proximally from a base that circumferentially surrounds the port on the proximal side of the transverse wall portion, the shield being configured so as to provide a guide for the insertion of a hypodermic needle into the port; and
- a light source contacting the base of the shield and radially spaced from the lumen, and selectively operable to illuminate at least a portion of the shield.

2. The cap adapter of claim 1, wherein the light source comprises a light-emitting diode (LED).

3. The cap adapter of claim 2, wherein the LED is selectively connectable to a power source located in the base radially spaced from the lumen so that the LED may be repeatedly illuminated and darkened.

4. The cap adapter of claim 3, wherein a selective connection between the LED and the power source comprises a conductive material configured to close a circuit between the LED and the power source in response to pressure applied to the base of the shield.

5. The cap adapter of claim 3, further comprising a removable insulating material interposed between electrical contacts on the LED and electrical contacts on the power source.

6. The cap adapter of claim 1, further comprising a spike extending distally from the wall portion, the spike defining a second lumen passing through the wall portion, the second lumen being spaced from and not in fluid communication with the first lumen, the spike including a sharp distal tip configured to pierce the sealing stopper on the vial.

7. The cap adapter of claim 1, further comprising a secondary sealing member abutting a distal face of the wall portion and sealing a distal end of the lumen.

8. The cap adapter of claim 1, wherein the vial-engaging portion comprises a plurality of clamping members that are circumferentially spaced about an edge of the wall portion and cantilevered distally from the wall portion, the clamping members being configured to snap fit about the mouth of the vial to secure the cap adapter to the vial.

9. The cap adapter of claim 1, further comprising a locking sleeve surrounding at least a portion of the vial-engaging portion.

10. The cap adapter of claim 9, wherein an inner surface of the locking sleeve includes at least one elevated surface configured to engage the vial-engaging portion.

11. The cap adapter of claim 10, wherein the vial-engaging portion and the locking sleeve are rotatable with respect to one another between an unlocked position and a locked position.

12. The cap adapter of claim 10, wherein the locking sleeve includes at least one locking surface configured to bear against the vial-engaging portion to prevent relative rotation of the vial-engaging portion and the locking sleeve from the locked position to the unlocked position.

13. The cap adapter of claim 10, wherein the locking sleeve includes at least one lip configured to bear against the vial-engaging portion to resist, but not prevent, relative rotation of the vial-engaging portion and the locking sleeve from the locked position to the unlocked position.

14. The cap adapter of claim 1, wherein the shield flares radially outward from the port.

15. The cap adapter of claim 1, wherein the light source comprises a chemiluminescent member.

16. The cap adapter of claim 15, wherein the chemiluminescent member is operable to emit light in response to the application of pressure thereto.

17. The cap adapter of claim 15, wherein the chemiluminescent member comprises a ring positioned around the base of the shield.

18. The cap adapter of claim 1, further comprising a spike extending distally from the wall portion, the spike defining an extension of the lumen and including a distal tip configured to pierce the sealing stopper on the vial.

* * * * *